US009102977B2

(12) United States Patent
Kjaerulff et al.

(10) Patent No.: US 9,102,977 B2
(45) Date of Patent: Aug. 11, 2015

(54) METHOD FOR ANALYSIS OF CELLULAR DNA CONTENT

(75) Inventors: Søren Kjaerulff, Hillerød (DK); Martin Glensbjerg, Brønshøj (DK)

(73) Assignee: ChemoMetec A/S, Allerød (DK)

( * ) Notice: Subject to any disclaimer, the term of this patent is extended or adjusted under 35 U.S.C. 154(b) by 0 days.

(21) Appl. No.: 13/577,955

(22) PCT Filed: Feb. 10, 2011

(86) PCT No.: PCT/DK2011/050037
§ 371 (c)(1), (2), (4) Date: Oct. 29, 2012

(87) PCT Pub. No.: WO2011/098085
PCT Pub. Date: Aug. 18, 2011

(65) Prior Publication Data
US 2013/0045485 A1 Feb. 21, 2013

Related U.S. Application Data

(60) Provisional application No. 61/303,412, filed on Feb. 11, 2010.

(30) Foreign Application Priority Data

Feb. 11, 2010 (DK) ................................. 2010 70047

(51) Int. Cl.
*C12Q 1/68* (2006.01)
*C12M 1/34* (2006.01)
*G01N 21/64* (2006.01)
(Continued)

(52) U.S. Cl.
CPC .......... *C12Q 1/6806* (2013.01); *G01N 21/6428* (2013.01); *C12Q 1/6895* (2013.01); *G01N 2021/6439* (2013.01)

(58) Field of Classification Search
CPC .... C12Q 1/6806; C12Q 1/68; G01N 21/6428; G01N 21/6328; G01N 21/64
USPC ............. 435/6.1, 6.14, 287.2; 422/82.08, 430
See application file for complete search history.

(56) References Cited

U.S. PATENT DOCUMENTS 5,770,363 A * 6/1998 Brown ......................... 435/6.19
6,221,623 B1 * 4/2001 Smith-McCune et al. ... 435/7.23
2004/0157211 A1 * 8/2004 Skyggebjerg et al. ............ 435/5

OTHER PUBLICATIONS

Myc et al, DNA Stainability in Aneuploid Breast Tumors: Comparison of Four DNA Fluorochromes Differing in Binding Properties, 1992, Cytometry, 13, 389-394.*

(Continued)

*Primary Examiner* — Narayan Bhat
(74) *Attorney, Agent, or Firm* — Gifford, Krass, Sprinkle, Anderson & Citkowski, P.C.

(57) ABSTRACT

Disclosed is a fast and simple method for quantification of nucleic acid of biological cells as 2-step protocol. In the first step cells are treated with an acidic solution containing a non-ionic detergent and a fluorescent DNA specific label. In the second step the sample may be neutralized. Determining of the content of nucleic can be performed by fluorescence microscopy. The method may also be used for obtaining information of cell cycle analysis, ploidy determination, measurements of nucleotide incorporation and assays for proliferation, health, stress level, apoptosis, necrosis, or other state of conditions of cells. The invention also relates to a kit of parts comprising an acidic agent, a detergent, a labelling agent and optionally a neutralization agent.

17 Claims, 3 Drawing Sheets

(51) Int. Cl.
*G01N 21/66* (2006.01)
*G01N 31/22* (2006.01)
*G01N 33/52* (2006.01)

(56) References Cited

OTHER PUBLICATIONS

Ahern, Biochemical, Reagents Kits Offer Scientists Good Return on Investment, 1995, The Scientist,9, p. 20.*
Freestone et al, The Mammalian Neuroendocrine Hormone Norepinephrine Supplies Iron for Bacterial Growth in the Presence of Transferrin or Lactoferrin, 2000, Journal of Bacteriology, 182, 6091-6098.*
Bano et al, Detection and partial characterization of adenocarcinomas. collagen synthesis stimulating activities in rat mammary adenocarcinomas, J. Biol. Chem. 1983, 258:2729-2735.*
Laakso et al, Biodegradable Microspheres VI: Lysosomal Release of Covalently Bound Antiparasitic Drugs from Starch Microparticles, 1987, Journal of Pharmaceutical Science, 76, 134-140.*
Drechsel et al, Purification and chemical characterization of staphyloferrin B, a hydrophilic siderophore from *Staphylococci*, 1993, BioMetals, 6,185-192.*
Wlodkowic D., et al., "SYTO Probes in the Cytometry of Tumor Cell Death," Cytometry, 73A(6):496-507, 2008.
Darzynkiewicz Z., et al., "Determining Cell Cycle Stages by Flow Cytometry," Current Protocols in Cell Biology, 8.4.1-8.4.18, 1999.
Lin A.A., et al., "A Rapid Method for Counting Cell Nuclei Using a Particle Sizer/Counter," Biotechnology Techniques 5 (2):153-156, 1991.
Otto F.J., "High-Resolution Analysis of Nuclear DNA Employing the Fluorochrome DAPI," In: Darzynkiewicz Z., Robinson J.P., Crissman H.A.: "Methods in Cell Biology" 41:211-217, 1994.
Anonymous, "SYTO RNASelect™ Green Fluorescent Cell Stain (S32703)," Retrieved from the Internet: URL:http://probes.invitrogen.com/media/pis/mp32703.pdf [retrieved on Sep. 2, 2010], 2004.
DeCoster M.A., "The Nuclear Area Factor (NAF): A Measure for Cell Apoptosis Using Microscopy and Image Analysis," In: A. Méndez-Vilas, J. Díaz: "Modern Research and Educational Topics in Microscopy," Formatex, Internet, 378-384, 2007.
Boisen Sthen, "Precise and Objective Cell Counting," BIOforum Europe 38-39, Retrieved from the Internet: URL: http://www.chemometec.com/en-GB/Knowledge-Bank/Publications/Mammalian-Cells.aspx [retrieved on Aug. 20, 2010], 2005.
Long, X. et al., Flow Cytometric Analysis of Green-Fluorescent Nucleic Acid Stains in Brain Tumor Cells, *China Academic Journal Electronic Publishing House*, pp. 231-235, 2009.

* cited by examiner

METHOD FOR ANALYSIS OF CELLULAR DNA CONTENT

All patent and non-patent references cited in the application, or in the present application, are also hereby incorporated by reference in their entirety.

FIELD OF INVENTION

The present invention relates to a method for determining the amount of nucleic acid of biological cells. The method is simple, rapid and reliable for analysing and quantifying the DNA or DNA and RNA content of biological cells. The method described herein is based on lysing biological cells by adding acid to a sample, labelling the nucleic acid and optionally neutralising the sample before examination of the labelled nucleic acid. The method is especially suited to be used with fluorophores capable of identifying DNA and/or RNA as the labelling agent. The method can for example be used for cell cycle analysis, ploidy determination and assays for proliferation, health, stress level, apoptosis, necrosis, or other state of conditions of cells. The invention also relates to an apparatus for determining the amount of nucleic acid of biological cells and to a cassette used in the apparatus. The invention also relates to a kit of parts for use in determining the amount of nucleic acid of biological cells.

BACKGROUND OF INVENTION

Characterizing cell viability and other cell features can provide useful information with respect to a wide range of applications. However, methods presently employed are quite complex and time consuming. The cell cycle represents the most fundamental and important process in eukaryotic cells. Being an ordered set of events, culminating in cell growth and division into two daughter cells, the cell cycle is tightly regulated by defined temporal and spatial expression, localization and destruction of several cell cycle regulators. Cyclins and cyclin-dependent kinases (CDK) are major control switches for the cell cycle, causing the cell to move from $G_1$ to S or $G_2$ to M phases. In a given population, cells will be distributed among three major phases of cell cycle: $G_1/G_0$ phase (one set of paired chromosomes per cell), S phase (DNA synthesis with variable amount of DNA), and G/M phase (two sets of paired 2 chromosomes per cell, prior to cell division).

Because cell cycle dysregulation is such a common occurrence in neoplasia, the opportunity to discover new targets for anticancer agents and improved therapeutics has been the focus of intense interest. The cell cycle analysis has applicability to a variety of areas of life science research and drug development, including cancer biology, apoptosis analysis, drug screening and measuring health status of cell cultures, e.g. in bioreactors.

The most common approach to determine the cell cycle stage is based on measurement of cellular DNA content. DNA content can be determined using fluorescent, DNA-selective stains that exhibit emission signals proportional to DNA mass. Cellular fluorescence is measured by flow, image or laser scanning cytometry. A variety of fluorochromes can be used for staining of DNA.

DNA staining is typically performed on cells permeabilized with either non-ionic detergents or alcohol fixation. A plethora of protocols based on these two approaches for cell permeabilization have been published in the literature. Although most of these protocols are relatively simple and applicable for many cell types they have several drawbacks and limitations. Firstly, the prior art methods require that cells are in suspension and, accordingly, adherent cells lines have to be detached prior to analysis. Secondly, they contain washing steps, calling for centrifugation that often results in cell loss. Thirdly, they promote cell aggregation, which hampers DNA content quantification of individually cells.

The method described herein is a simple method for quantification DNA and/or RNA of individually cells by releasing nuclei from the cells and performing nucleic acid quantification on these nuclei.

A widely used method to monitor cell concentration of adherent cells is to count released nuclei. Release of nuclei is often achieved using solutions containing mild detergents, such as Triton-X100. It has been described that Triton X-100 in combination with citric acid efficiently releases nuclei from anchorage-dependent cultures and cultures containing cell aggregates (Lin et al., A rapid method for counting cell nuclei using a particle sizer/counter (1991). Biotechnology Techniques, 5, 153-156). Lin et al used a solution of 100 mM citric acid, 1% triton X-100 and 0.1 mg/ml crystal violet. This solution has a pH value below 2, and a non-fluorescent dye. The method of Lin et al is used for cell counting and not for determining the amount of nucleic acid within the nuclei.

When quantifying nucleic acid of nuclei to assess stages of cell cycle, it is important to obtain results without to much "noise". The invention described herein makes it possible to obtain good results from labelled nucleic acid at low magnification and with a low degree of noise.

SUMMARY OF INVENTION

The method presented here provides a simple, rapid and robust method for analysing and quantifying the DNA content of cells. The preferred method is a 2-step protocol. In the first step cells are treated briefly with a weakly acidic solution containing a non-ionic detergent and a DNA specific dye, such as DAPI. This treatment causes efficient detaching of cell nuclei from the cells, declumping and homogeneous staining of the nucleic acid of the sample. In the second step the sample may be neutralised by adding a weakly basic solution. After neutralisation of the sample cellular fluorescence can be directly quantified using flow, image or laser scanning cytometry.

It has surprisingly been found that when treating cells by the method described herein, it is possible to obtain cell nuclei with labeled nucleic acid wherein the amount of nucleic acid within the nuclei can easily be detected even at low magnification of microscope equipment. The method as described herein results in
  cell nuclei with only little or no aggregation,
  a liquid consistence of the sample making it easy to analyze the sample,
  cell nuclei which give rise to sharp peaks of G0/G1 or G2 phases when illustrating nucleic content profiles of the labeled nuclei,
  cell nuclei which give rise to a reduced CV of the peaks,
and the method is simple and fast and gives reliable results.

The invention thus relates to a method for quantification of nucleic acid of at least one biological cell, where the method comprises the steps of
  i. Providing a sample comprising at least one biological cell, or providing a sample comprising cell parts with nucleic acid, said cell parts being obtained from at least one biological cell,
  ii. Adding an acidic agent to the sample causing acidification of the sample to a pH level between 2.0 and 3.0,
  iii. Adding a detergent to the sample causing lysis of the biological cell, iv. Adding a fluorescent labelling agent to the sample, wherein the fluorescent labelling agent interacts with nucleic acid, obtaining a sample with labelled nucleic acid, v. Determining the content of fluorescent labelled nucleic acid of the at least one biological cell or cell parts in the sample.

The acidic agent preferably lowers the pH of the sample to a pH of 1.5-4.5, such as to a pH level between 2.0 and 3.0. The lowered pH together with the detergent results in a release of cell nuclei from the cells. After cell nuclei are released the nucleic acid of these nuclei are labelled preferably with a fluorophore. An analysis bases on fluorescence can reveal the amount of nucleic acid present in the nuclei.

The method may also be used for obtaining information of cell cycle analysis, ploidy determination, measurements of nucleotide incorporation and assays for proliferation, health, stress level, apoptosis, necrosis, or other state of conditions of cells.

The invention also relates to a kit of parts for use in the method described herein, where the kit comprises A volume of an acidic agent,
A volume of a detergent,
A volume of a fluorescent labelling agent capable of interacting with nucleic acid, and
Optionally a volume of a neutralization agent.

A composition for lysing and labelling biological cells, said composition comprising An acidic agent or an acid buffer,
A detergent and
A fluorescent labelling agent.

Another composition may be a composition for labelling biological cells and simultaneously neutralising a sample comprising the biological cells, wherein the composition comprises A fluorescent labelling agent and
A neutralisation agent.

The method is simple and fast, and results can be obtained within few minutes from loading an apparatus including a fluorescence microscope combined with image analysis software, a flow cytometer and a laser scanning cytometer.

The method can be used for analysing the development of a disease causing unstable cells of an individual, where the method comprises the steps of, at two different points of time a. Obtaining a biological sample from an individual,
b. Analysing the obtained biological sample for the presence of unstable cells,
c. Comparing the number of unstable cells identified in the biological sample at the two different points of time,
d. Determining the development of the disease based on the comparison of the number of unstable cells identified in the two biological samples.

The method is especially suited to monitor the development of cancer diseases or diseases amending cells of the blood.

SHORT DESCRIPTION OF DRAWINGS

DETAILED DESCRIPTION OF THE INVENTION

Figure 1:
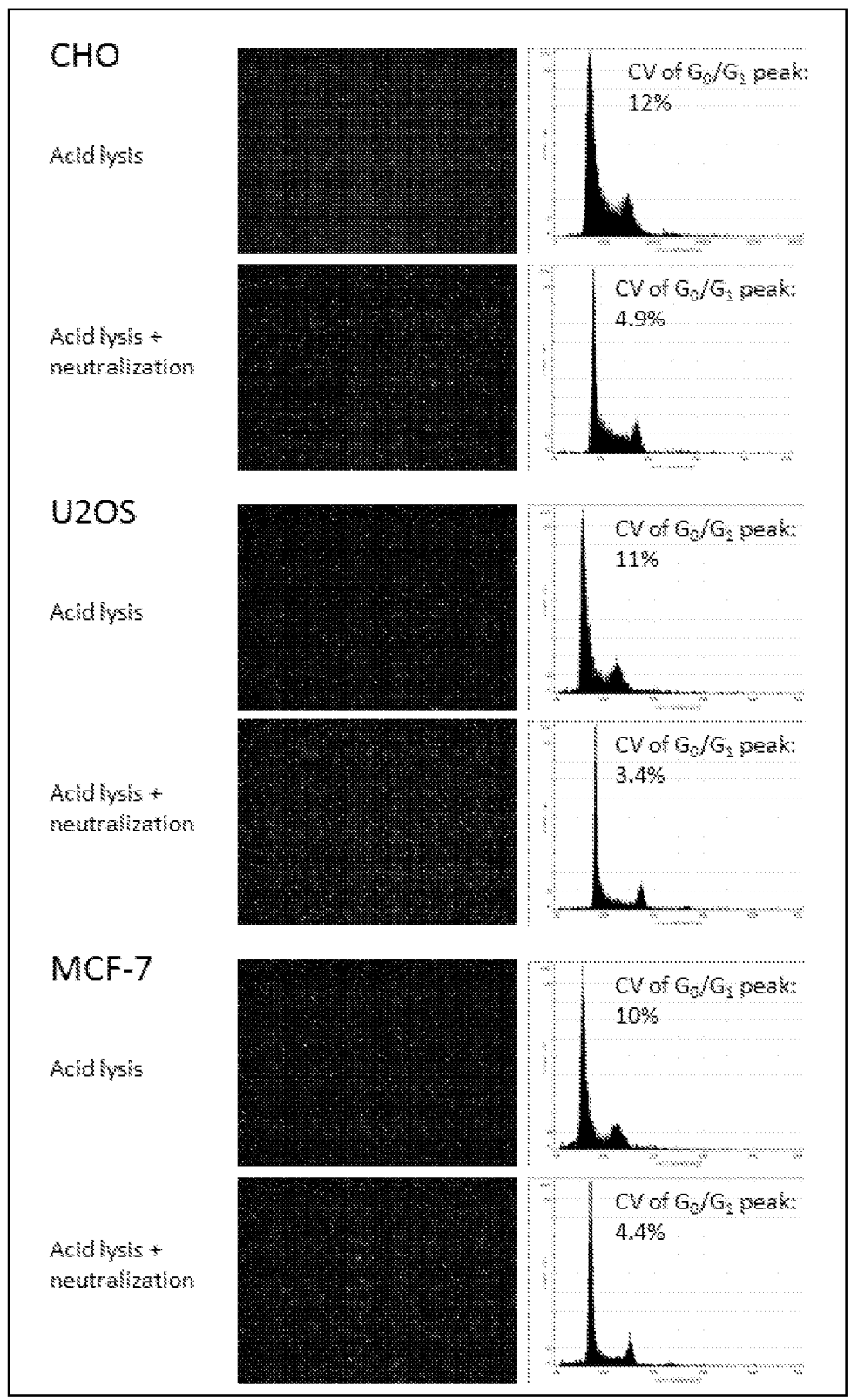
FIG. 1 illustrates DNA content profiles of nuclei of different cell types, where the nuclei are released by acid lysis and stained with DAPI.

The method described herein allows detaching, permeabilization, declumping and homogenous staining of biological cells in a cell population. In a simple form, the method can be performed in two simple steps without any washing and/or without any centrifugation.

In an aspect the invention relates to a method for quantification of nucleic acid of at least one biological cell, wherein the method comprises the steps of i. Providing a sample comprising at least one biological cell, or providing a sample comprising cell parts with nucleic acid, said cell parts being obtained from at least one biological cell,
ii. Adding an acidic agent to the sample causing acidification of the sample,
iii. Adding a detergent to the sample causing lysis of the biological cell,
iv. Adding a fluorescent labelling agent to the sample, wherein the fluorescent labelling agent interacts with nucleic acid, obtaining a sample with fluorescent labelled nucleic acid,
v. Determining the content of fluorescent labelled nucleic acid of the at least one biological cell or cell parts in the sample.

As described below the acidic agent and the detergent may be added simultaneously to the sample, hereby reducing the above mentioned three-step method to a simpler two-step method. The labelling agent can be added together with the acidic agent and the detergent, or can be added afterwards. A neutralisation agent can be added together with the labelling agent or after nucleic acid has been labelled by the labelling agent. The content of labelled nucleic acid can be determined e.g. by flow cytometry, laser scanning microscopy and fluorescence microscopy e.g. in a system comprising a fluorescence microscope and imaging and processing means capable of analysing the data obtained from the labelled biological sample.

Sample

The sample to be analysed by the method described herein may be any sample, such as a biological sample, comprising cells for which the amount of nucleic acid should be determined. A determination of the amount of nucleic acid of cells can be used for several purposes, some of these are cell cycle analysis, ploidy determination, measurements of nucleotide incorporation and assays for proliferation, health, stress level, apoptosis, necrosis, or other state of conditions of cells.

By the term "amount of nucleic acid" is generally meant the nucleic acid present in the nucleus of the cells, although it can also be the entire amount of nucleic acid within the nucleus and in other organelles. In respect of cells without a nucleus (prokaryotes) the "amount of nucleic acid" is the entire content of nucleic acid of the cell.

In particular a biological sample may be selected from a body fluid sample, a tissue sample, a fermentation sample, a liquid cultivation sample, a cell culture sample, a water sample, such as mammalian and yeast cell cultures, a beverage sample, a pharmaceutical sample, cells suspended in a liquid and from cells producing therapeutic proteins.

More particular the biological sample is selected from a blood sample, a urine sample, a saliva sample, a semen sample, a solubilised tissue sample, a milk sample a cerebrospinal fluid or lymph. The biological sample can also be selected from a liver sample, a kidney sample, a muscle sample, a brain sample, or a lung sample.

The biological sample may be selected from any species, such as a human sample, a mouse sample, a rat sample, a monkey sample, a dog sample.

Furthermore, the sample may be selected from a culture of cells, such as a bacterial culture, a mammalian cell culture, a protozoa culture or other cell cultures.

A sample representing a biological material can be taken from raw material and processes associated with the manufacture, storage and transportation of said biological material.

A sample to be analysed may comprise at least one biological cell, or the sample may comprise cell parts with nucleic acid, where the cell parts are obtained from at least one biological cell. Cell parts may e.g. be nuclei isolated from any type of cells, or cell parts may e.g. be protoplasts or spheroplasts obtained from plant cells, bacterial cells or fungal cells.

The biological cells of any of the samples mentioned herein may be prokaryotes. In respect of prokaryotes, which do not have nuclei, the amount of nucleic acid which is to be labelled according to the method described herein is the entire nucleic acid of the cell. When treating prokaryotes with the acid agent and the detergent as described herein without removing the cell membrane, this cell membrane prevents the release of the nucleic acid of the cell making it possible to analyse single cells. Preferably the cells to be analysed with the method described herein are cells without a cell wall.

Preferably the biological cells to be analysed are eukaryotes. Eukaryotes may be selected from the group of protozoa, fungi, bacteria, animal cells and plant cells.

The sample obtained from fungi can be obtained from the group of fermenting organisms such as yeast—*Saccharomyces cerevisiae, Schizosaccharomyces pombe, Hansenula polymorpha, Pichia pastoris, Pichia methanolica, candida albicans*; from filamentous fungi such as *Aspergillus niger, Aspergillus nidulans, Aspergillus oryzae, Penicillium chrysogenum*.

The method is especially suitable for the yeasts *Saccharomyces cerevisiae* and *Schizosaccharomyces pombe*, since these two species are used as model systems for cell cycle control.

Preferably the animal cells to be used with the method described herein are mammal cells.

The animal cells may be obtained from a sample which is a biological sample selected from a blood sample, a urine sample, a saliva sample, a semen sample, a solubilised tissue sample and a milk sample.

The animal cells may also be obtained from a sample which is a biological sample selected from a liver sample, a kidney sample, a muscle sample, a brain sample and a lung sample.

The mammal cells may be selected from the group of cell lines, tissue, somatic cells, blood, animal semen, milk, epithelial cells, adipocytes, hybridomas.

Examples of mammal cells which can be analysed by the method described herein are cell lines from the group of CHO (Chinese hamster ovary (CHO) cells); MCF-7 (a breast cancer cell line); U2OS (human osteosarcoma cells cultivated from bone tissue); Jurkat cells; HeLa (human cervical cancer cell line); HEK-293 (Human kidney cell line); COS-7 (African green monkey kidney cell line); MDCK (Dog kidney cell line); NIH-3T3 (Mouse embryonic cell line) and Schneider S2 (Fruit fly cell line) cells. The acid lysis method described herein has been validated on all the above mentioned cells types with similar results. However, not all of these experiments are presented herein.

Preferred cell lines to be analysed include HepG2 (human hepatocytoma cell line), Hep2 (human laryngeal cell line), KB (human pharyngeal cell line), U87 (glioblastoma-astrocytoma cell line), Saos-2 (Osteosarcoma), YAR (EBV transformed B-cells), Vero (African green monkey kidney cell line), BHK-21 (Hamster kidney cell line) and Sf9 (Insect (*Spodoptera frugiperda*) kidney cell line).

The animal cells may be selected from any animal e.g. from an animal of the group of mouse, rat, monkey, dog, fish, cow/cattle, insect, horse, cat, bird and pig.

The cells to be analysed may also be all kind of plant cells which. As an example plant cells may be selected from the group of leaf cells, pollen cells, egg cells, callus cells, and protoplasts. Plant cells may also be obtained from seedlings or from in vitro grown plants or plant organs.

Plant cells can be analysed without removing the cell wall. However, to obtain a good result i.e. a result based on analysis of individual cells, it is important that the cells are separated from each other before performing the analysis of the amount of nucleic acid within the cells.

When testing cells obtained from plants, it is also possible to perform the analysis on protoplast. Protoplasts can be produced by enzymatic degradation of the cell wall. Any enzyme normally used for removal of cell walls can be used to produce the protoplast analysed by the method described herein. It is not a requisite that the protoplasts are capable of regenerate into a plant cell or an entire plant as the method described herein is lethal to the biological cells.

When analysing plant cells it may be beneficial only to perform the analysis based on nuclei released from the cells. Hereby any possible signals from labelled nucleic acid of the organelles or other structures capable of binding the labelling agent present in the cytoplasm can be avoided.

A sample provided for analysis as described herein may be cells selected from the group of cells adhered to a solid support, in vitro growth plates, petri disches, cells cultured in T-flasks, Microtitres-plates, bioreactors, spinnerflasks, microcarriers (microcarrier beads), 3-D cultures, organ cultures and cells cultured in suspension.

Preferable the cells to be analysed with the method described herein are cells attached to a solid part. Before performing the analysis as described herein the cells are released from the solid part or the cell nuclei are released from the cell membranes attached to the solid part.

Release of Cells

The sample containing biological cells to be analysed by the method described herein, may be obtained as cells cultivated on a solid part, or it may be cells from a tissue of animal or plant origin, or the cells may be in a liquid sample e.g. a liquid sample obtained from a mammal. More sample types are described elsewhere herein. Before adding an acidic agent to the biological cells, the cells may be released from a solid part, or the cells may be released from the tissue. However, in a preferred embodiment the entire cells need not be in suspension to perform the analysis as described herein.

Cells cultured on a solid part or a solid support may be released from this solid part by treatment with trypsin, collagenases, dispase or isotonic solutions supplemented with a chelating agent, such as EDTA and versene. However, in a preferred embodiment the cells are not released from the solid part prior to release of cell nuclei by the addition of an acidic agent and a neutralisation agent of the method described herein. Hereby a step of trypsination need not be present in the method. Cell nuclei can be released directly from the cells cultured on the solid part.

When working with a tissue, the tissue can be homogenised e.g. by tissue homogenization, e.g. using a Potter-Elvehjem tissue grinder with a pestle. The homogenised tissue can be analysed by the method as described herein.

In respect of cells obtained as a tissue sample, it is also possible to treat one or more tissue parts directly with the acidic agent and/or the detergent to release cell nuclei from the tissue. The tissue may be placed in a liquid e.g. water before performing the reaction with the acidic agent and/or the detergent. After release of the nuclei remaining tissue may be removed e.g. by filtration and the released nuclei can be obtained as part of the filtrated liquid. Liquid may be removed from the nuclei as described elsewhere herein.

When the sample with the biological cells to be analysed comprises culture medium or is a liquid sample obtained e.g. from a mammal, this culture medium or liquid medium can be removed from the cells or cell parts before or after the treatment with the acidic agent.

Removal of the culture medium or the liquid medium e.g. before adding the acidic agent, can be performed by pouring away the liquid part, removal of the liquid part by pipette, filtration, sedimentation, or centrifugation.

A washing step of the cells or cell parts can be performed before adding an acidic agent to the sample. Preferably a washing step is performed after the culture medium is removed. By washing the cells and/or nuclei some structures which can be capable of interacting with the labelling agent (such as a dye, or fluorochrome) can be removed from the sample. Hereby the result is improved as the signals from these structures are avoided. However, in a preferred embodiment the method as described herein is performed without a washing step.

A washing step can be performed with a washing solution. A washing solution may be selected from the group of balanced salt solutions, such as Phosphate Buffered Saline (PBS), Hanks' Balanced Salt Solution (HBSS) and Earle's Balanced Salt Solution (EBSS). PBS (Phosphate buffered saline) is a preferred washing solution.

Example 4 as described below demonstrates that the method can be used for efficient release and staining of nuclei from cells attached to different materials, such as T-flasks, microtiter plates and micro-carriers.

Example 5 as described below demonstrates that the method, in addition to attached cells, can be used for suspension cells, as well as adherent cells broad into suspension.

Acidifying the Sample

In a preferred embodiment the sample with biological cells or cell parts is acidified by adding an acidic agent. By reducing the pH of the sample as described herein, the nucleic acid of the biological cells condense, and the lowered pH value makes it possible to analyse separate nuclei in a true fluid liquid. If performing the method without adding an acidic agent, the liquid becomes less fluid and more difficult to handle i.e. it becomes more difficult to obtain separate nuclei to analyse. Without adding the acidic agent the consistence of the sample can be described as "viscous".

The acidic agent to be added to the sample is preferably in a liquid form. However, acidic salts can also be used as the acidic agent. A liquid form of the acidic agent is preferred as this makes it easier to adjust the pH of the sample to the correct value compared to lowering the pH with an acidic salt.

The acidic agent can be selected from the group of biological buffers of citric acid, citrate buffer, phosphoric acid, maleate, phosphate, glycine, glycylglycine, malate, lactate, formate, succinate, acetate and propionate.

Preferred buffers are citrate, maleate, phosphate, glycine, glycylglycine, malate and lactate. Further preferred buffers are citrate and phosphate.

In a preferred embodiment the acid agent as described above is added to the sample in an amount suitable to obtain a pH-value of the acidified sample in the range of 1.5-4.5. Preferable the pH of the sample is lowered to 1.7-4.0. Further preferred is a pH-value of 1.8-3.5. Even more preferred is a pH-value of 2.0-3.0, further preferred 2.1-2.9, more preferable 2.2-2.8. The pH range can also be 2.3-2.7; 2.4-2.6; 2.45-2.55 or the pH can be about 2.5. If reducing the pH to below 2 such as to a pH of 1.5 there is a risk that DNA and/or RNA is destroyed. This will reduce the value of the analysis performed when examining the content of labelled nucleic acid. If the pH-value is too high i.e. above 3, e.g. 4.5, the sample will be viscous and the cells may adhere to each other, which reduces the ability to obtain a good analysis.

In a preferred embodiment the pH of the acidified sample is kept under acidic conditions for a period of about 1-30 min, such as 1.5-20 min, e.g. 2.5-10 min, such as 3-8 min, e.g. 3.5 min-7 min. Preferably the acidic condition is upheld for about 4 minutes to about 6 min. More preferably the acidic condition is upheld for about 5 minutes.

The acidic agent is preferably a liquid solution with any of the mentioned buffers in a concentration in the range of 25-250 mM, preferably in the range of 50-200 mM, more preferably 75-150 mM, most preferred the concentration is about 100 mM.

The amount of acidic agent used for acidifying the sample with the nuclei may be any amount. However, it is the pH-value of the acidified sample which is of importance when adding the acidic agent to the sample. The pH-value of the acidified sample should preferably be as described above.

In a preferred embodiment the acidifying step is performed without a hydrolysis of the nucleic acid as this will result in an inaccurate DNA quantification.

In another preferred embodiment the sample trypsination is not performed as part of the method.

In a further preferred embodiment the sample with the nuclei is not subjected to fixation of cells. Thus a fixation step may be omitted i.e. not be present before, under or after the acidifying step. Especially preferred is when a fixation step performed with alcohol such as 50-96% alcohol e.g. 70% alcohol is not performed.

Lysis of Cells—Detergent

In a preferred embodiment a detergent is added to the sample. The detergent permeabilises or lysis the plasma membrane and maintains the cell nuclei intact. By permeabilising or lysing the plasma membrane it is possible to have the cell nuclei released from the cells.

The detergent can be added to the sample simultaneously with the acidic agent, or after adding the acidic agent e.g. when the sample has been kept at the lowered pH for at least 1 min, such as for at least 2 min, e.g. for at least 3 min, such as for at least 4 min, e.g. for at least 5 min, such as for at least 6 min, e.g. for at least 8 min.

The detergent can be selected from the group of Triton X-15, Triton X-45, Triton X-100, Triton X-102, Triton X-114, Triton X-207, Triton N-57, Triton N-101, Triton QS-158, Triton 770, Igepal CA-630, NP-40, Brij-35, Brij 96, Tween-20, Tween-80, CHAPS, Cetyl, Cetyl-N3. Luten-Sol, Losec and Pluronic L31.

The following detergents are all non-ionic and are preferred detergents Triton X-15, Triton X-100, Triton X-114, Triton N-57, Triton N-101, Triton QS-158, Igepal CA-630, NP-40 and Brij 96.

The detergent as described herein is preferably used as a liquid with a detergent concentration of 0.05%-5% (w/v), more preferred of 0.06%-4%, further preferred of 0.07-3.5%, yet further preferred of 0.08%-3%, even more preferred of 0.09%-2.5%, most preferred of 0.1-2%. The concentration can thus also be in the range of 0.1%-0.5%, 0.5%-1%, 1%-1.5% or 1.5%-2%.

More preferred is when the amount of detergent used constitute 0.05%-5% (w/v) of the amount of the acidic agent, more preferred of 0.06%-4%, further preferred of 0.07-3.5%, yet further preferred of 0.08%-3%, even more preferred of 0.09%-2.5%, most preferred of 0.1-2%. The concentration of the detergent in relation to the amount of the acidic agent can thus also be in the range of 0.1%-0.5%, 0.5%-1%, 1%-1.5% or 1.5%-2%.

In a preferred embodiment the detergent is present in a liquid together with the acidic agent. The concentration of the acidic agent can be anyone as described above, and the concentration of the detergent can also be anyone as described above. Preferably the concentration of the acidic agent is 75-150 mM, and the detergent is added in an amount to constitute 0.08%-3% of the liquid composition. Further preferred is a liquid composition with a concentration of an acidic agent of about 100 mM and a detergent of 0.1-2%.

In example 1 it is illustrated that nuclei released using acid lysis (citric acid+non-ionic detergent) can be homogenously stained with the DNA specific dye DAPI and used for obtaining DNA content profiles by quantitative cytometry. The results of example 1 further show that the accuracy and precision of the method can be significantly improved if the acid released nuclei are neutralized prior to analysis.

In example 2 presented below the optimal pH range for nuclei release, de-aggregation and homogeneous DNA staining was determined. Standard protocols for staining cellular DNA describe buffers with neutral pH (see for example, Darzynkiewiez, Z., et al. (2001) Current Protocols in Cell Biology, Eds. Bonifacino, J. S., et al., John Wiley & Sons). However, for efficient release of nuclei, without aggregation and at the same time achieving highly homogeneous DNA staining it was revealed that acidic conditions are beneficial. Optimal pH seems to be 2.2-2.8 for all three criteria to be fulfilled.

Labelling Nucleic Acid

The nucleic acid of the biological cells is labelled with a labelling agent.

In a preferred embodiment the labelling agent comprises a chemical group capable of emitting fluorescent light. A system based on fluorescence is generally more sensitive than a chromogenic since fewer product molecules are necessary for providing enough electromagnetic radiation to visualise the cells.

A fluorescent label as a labelling agent is preferably capable of emitting signals in the wavelength range of from 300 to 1200 nm when excited by excitation light, the emitted signal may have a wavelength between 300 nm to 800 nm, or between 300 nm to 400 nm, or between 400 nm to 500 nm, or between 500 nm to 600 nm, or between 600 nm to 700 nm, or between 700 nm to 800 nm. One preferred fluorescence method is the method of polarised fluorescence.

The step of adding a labelling agent to the sample can be performed by adding a fluorescent labelling agent
  to the acidic agent before this is added to the sample,
  to the acidic sample,
  to the neutralization agent before this is added to the acidic sample, or
  to the neutralised sample.

Preferably the labelling agent is included in an acidic solution causing acidification of the sample when added to the sample and/or the labelling agent is included in a neutralization agent before this is added to the acidified sample. Preferred is when the labelling agent is added to only the acidifying solution or to the neutralization solution i.e. the labelling agent is not present in both the acidic solution and the neutralization solution. Thus in a preferred embodiment, the labelling agent is not included in both the acidic solution (i.e. the solution with the acidic agent) and in the solution with the neutralisation agent.

The labelling agent is preferably a fluorescent dye capable of interacting with nucleic acid. The dye can be selected from the group of DNA specific dyes and dyes binding DNA and RNA.

Preferably the dye is a fluorophore. The fluorophore may have the emission of light which is different when the fluorophore is in solution compared to when the fluorophore is bound to nucleic acid. Hereby it is possible by the use of a specific filter for filtering the emitted light, to reduce or eliminate signals from the liquid part of the labelled sample i.e. to reduce signals from the background.

DNA specific dyes can be selected from the group of DAPI, Hoechst 33342, Hoechst 33258, Hoechst 34580, Draq5 and Nuclear ID red. Preferred is DAPI. Avoiding signals for RNA by using DNA specific dyes can improve the results obtained. This can be important e.g. when assessing the amount of DNA for cell cycles analysis.

DAPI is particularly competent as dye for measurement of the cell cycle stage. Firstly, the intensity of fluorescence integrated over a DAPI stained cell is in stoichiometric relationship to DNA content. Secondly, DAPI preferentially binds to double stranded DNA and the quantum yield of DAPI/RNA complexes is only 20% of that of the DAPI/DNA complex. Hence, using DAPI there is no requirement for removing RNA by RNase treatment prior to DNA content measurements. This is a prerequisite for other dyes commonly used for measurements of cellular DNA content, such as propidium iodide. DAPI interacts with double stranded DNA by associating with AT clusters in the minor groove. When bound to double-stranded DNA its absorption maximum is at 358 nm and its emission maximum is at 461 nm. Binding of DAPI to DNA produces a 20-fold fluorescence enhancement. Hence, excitation of DAPI requires a UV light source.

Dyes binding both DNA and RNA can be selected from the group of propidium iodide, 7-AAD, ethidium bromide, ethidium homodimer 1, ethidium homodimer 2, Acridine orange, LDS 751. Preferred is propidium iodide.

The dye can also be an RNA specific dye. RNA specific dyes can be selected from the group of 4"-6-bis(2"-imidazolinyl-4'-5'H)-2-phenyl-4'-phenoxindole, styryl RNA selective and SYTO® RNASelect™ Green.

When an analysis need to be based on the amount of RNA, the method as described herein can further comprise the step of adding DNAse to the neutralized sample followed by a step of labelling/staining with dyes binding both DNA and RNA. Hereby a wide range of fluorophores are available when compared to a method of specifically labelling the RNA only. To avoid destroying the enzyme activity of DNAse, the sample should preferably be neutralised before performing the enzyme reaction. The enzyme reaction is thus preferably to follow a neutralisation step. A DNAse reaction may be performed for about 30 minutes, such as from 25-40 min.

The amount of labelling agent (dye or fluorophore) is preferably adjusted to be 1-50 µg/ml as a final concentration of the sample containing the nucleic acid to be labelled. More preferably the amount of the labelling agent is 1-40 µg/ml, such as 2-30 µg/ml, e.g. 3-20 µg/ml, such as 4-10 µg/ml. If using DAPI, the final concentration of DAPI is preferably 1-20 µg/ml, more preferably 2-15 µg/ml further preferably 5-10 µg/ml. If using Propidium iodide the final concentration of Propidium iodide is preferably 2-40 µg/ml, more preferably 3-35 µg/ml, further preferably 4-30 µg/ml, most preferrably 5-25 µg/ml.

In example 3 it was illustrated that the method is very robust for variations in DAPI concentrations. Furthermore, it was shown that DAPI staining can be performed either in the lysis step or in the neutralization step. Both staining procedures allow specific and precise quantification of cellular DNA content.

Neutralisation of Sample

The sample is preferably neutralised by adding a neutralization agent before performing the analysis of the amount of nucleic acid in the nuclei or other cell parts.

In the method described herein, the method may comprise the further step of adding a neutralization agent. Addition of the neutralization agent may be performed after the sample has been treated by the detergent and before adding the label or the neutralization agent may be added after the sample has been treated by a labelling agent.

A neutralization step is optional. However, the neutralization step may be included to improve accuracy and precision of the method. Adding a neutralization agent is thus a preferred step of the method as described herein.

The neutralization agent may be selected from the group of biological buffers of citrate buffer, maleate, phosphate, glycine, glycylglycine, malate, succinate, carbonate, ethanolamine, DIPSO, Bis-Tris, ADA, ACES, imidazole, hydrazine, BES, HEPES, HEPPSO, HEPBS, AMP, AMPD, AMPSO, MES, MOPS, MOPSO, MOBS, PIPES, bicine, HEPPS, EPPS, POPSO, TAPS, TABS, TAPSO, borate, CHES, taurine, TEA, TES, tricine and tris.

Preferable the neutralization agent is selected from the group of maleate, phosphate, glycine, glycylglycine, malate, succinate, carbonate, Bis-Tris, ethanolamine, ADA, ACES, PIPES, MOPSO, imidazole, BES, MOPS, HEPES, TES, MOBS, DIPSO, TAPSO, TEA, HEPPSO, POPSO, tricine, hydrazine and tris.

The neutralisation buffer can have a pH between 7 and 9. Preferably the pH is 7.0-8.5, more preferably 7.0-7.5.

The concentration of the neutralization agent in a liquid solution can be 50-1000 mM, e.g. 60-900 mM, such as 70-800 mM, e.g. 80-700 mM, such as 90-600 mM. More preferred is a concentration of 100-500 mM.

The amount of neutralization agent used for neutralising the sample with the labelled nuclei may be any amount. However, it is the pH-value of the sample which is of importance when adding the neutralization agent to the sample. The pH-value of the neutralised sample should preferably be as described above.

Degradation of DNA or RNA

Degradation or disintegrating of RNA or DNA by adding RNase or DNase to the sample may be performed to obtain a signal only from the remaining part of the nucleic acid.

Degradation of DNA can be performed by adding DNase. In the labelling step any labelling agent in the form of a dye capable of interacting with nucleic acid can be added. Preferably the dye is a fluorophore as described elsewhere herein.

As described elsewhere herein, RNase is preferably added after neutralisation of the sample. To remove RNA, the preferred enzyme is RNase A. A final concentration of the RNase in the sample can be 0.05-5 mg/ml.

The step of degradation of RNA or DNA is preferably performed at or about a neutral pH-value of the sample. The pH optimum for the activity of the enzyme RNase A is 7.6, which is the most preferred pH of the sample when performing the RNA degradation with an RNase. However, the activity range of the enzyme RNase A is pH 6-10, which also reflects the preferred pH range when degrading RNA with an RNase.

The process of degradation of RNA or DNA is performed for at least 20 minutes, such as for about 25 minutes, e.g. about 30 minutes, such as about 35 minutes, e.g. about 40 minutes. Preferred is about 30 minutes.

Sample Volume

The optimal volume of the sample needed to perform the method and analysis as described herein is highly dependent on the number of cells or nuclei present in the sample and the predetermined statistical quality parameter sought.

Sample volumes may be from 0.005 µl up to several hundred milliliters. Thus, in one embodiment the sample volumes are from 0.01 to 20 µl, but often a volume of more than 0.1 µl, more than 1.0 µl or even more than 10 µl is used. In another embodiment the sample volume is from 0.02 µl to 1 ml.

If cells or nuclei from a sample with a large volume are to be analysed, then a smaller fraction of the sample can be extracted, and the method as described herein can be performed on the smaller fraction. When cells or from a large sample are retained, those cells can be re-suspended in a volume which is less than the volume of sample passed through the cell retaining means such as a filter.

Double Labelling

It is possible to perform a double labelling of the nucleic acid of the nuclei, which is to be analysed. The double labelling is performed with DNA specific and RNA specific labelling agent. These labelling agents can be present simultaneously when performing the labelling or the nucleic acid can be labelled first with one of the specific labelling agent and afterwards with the other one. The order of the labelling steps may be the exposure of the nuclei with a DNA specific labelling agent followed by an RNA specific labelling agent. The order may also be first an RNA specific labelling agent followed by exposure of the nuclei to a DNA specific labelling agent.

The labelling agents may be any one mentioned elsewhere herein. The concentration of the labelling agents and other features as described elsewhere herein in respect of labelling the nucleic acid is also relevant when performing a double labelling of a sample.

Obtaining Images of the Labelled Sample

Determining the content of labelled nucleic acid of the cells or cell parts in the sample can be performed by flow cytometry, laser scanning cytometry, image cytometry and microscopy, all of which can be performed with or without fluorescence.

The use of a technique involving fluorescence is preferred, as this is a sensitive system capable of giving good results even at low magnification. Thus, preferably the step of determining the content of labelled nucleic acid of the cells or cell parts in the sample is performed by a technique based on fluorescence. Hereby also the use of dyes which are capable of emitting fluorescence when illuminated with light is preferred.

A further step of the method described herein comprises assessing the result obtained when determining the content of labelled nucleic acid of the cells or cell parts in the sample to obtain information of the cells in respect of cell cycle analysis, ploidy determination, measurements of nucleotide incorporation and assays for proliferation, health, stress level, apoptosis, necrosis, or other state of conditions of cells. This step of assessing the results is performed after determining the content of labelled nucleic acid.

Preferred is assessing the result to obtain information of the cells in respect of cell cycle analysis, ploidy determination, incorporation of nucleotides, cell death such as apoptosis and necrosis.

Also preferred is assessing the result to obtain information of the cells in respect measurement of incorporation of nucleotides. More preferred is assessing the result to obtain information of cell cycle analysis. Most preferred is assessing the result to obtain information of ploidy determination of the nuclei.

The method may be combined with the TUNEL assay that detects late apoptotic cells by measuring the extent of DNA degradation. Terminal Transferase is used to mark the 3'-hydroxyl termini of DNA ends with BrdU. In general Terminal deoxynucleotidyl transferase dUTP nick end labeling (TUNEL) is a method for detecting DNA fragmentation by labeling the terminal end of nucleic acids. The TUNEL assay relies on the presence of nicks in the DNA which can be identified by terminal deoxynucleotidyl transferase, an enzyme that will catalyze the addition of dUTPs that are secondarily labeled with a marker. This marker may be a fluorophore, which can be the only fluorophore used in the method or it can be a different fluorophore than used for labelling the nucleic acid. The TUNEL assay may also label cells that have suffered severe DNA damage.

Fragmentation of DNA within cell nuclei will be rendered visible as a diagram with peaks in different areas than the main peak.

More preferred is assessing the result to obtain information of the cells in respect of cell cycle analysis, ploidy determination and incorporation of nucleotides. Most preferred is assessing the result to obtain information of the cells in respect of cell cycle analysis, ploidy determination and proliferation assays measuring incorporation of nucleotide analogs, such as BrdU and EdU.

BrdU=Bromodeoxyuridine (5-bromo-2-deoxyuridine) is a synthetic nucleoside that is an analogue of thymidine. BrdU is commonly used in the detection of proliferating cells in living tissues.

BrdU can be incorporated into the newly synthesized DNA of replicating cells (during the S phase of the cell cycle), substituting for thymidine during DNA replication.

Antibodies specific for BrdU can then be used to detect the incorporated chemical, thus indicating cells that were actively replicating their DNA. Binding of the antibody requires denaturation of the DNA, usually by exposing the cells to acid or heat. To visualise the antibodies, these antibodies can be labelled with a fluorophore before the antibodies bind to the BrdU or after the antibodies bind to the BrdU.

EdU (5-ethynyl-2'-deoxyuridine), is a nucleotide analog that incorporates similarly to BrdU as a thymidine analog. EdU reacts efficiently with an azide modified fluorescent dye to form a covalent bond, thus labelling replicating DNA. Compared to BrdU based assays EdU assays are in general simpler and faster.

A further step of the method as described herein may be a step of measuring the area of the nuclei. Measuring the area of the nuclei can be performed simultaneously with measuring the amount of labelled nucleic acid.

The area of the nuclei can be used to distinguish between different cell types of a sample with nuclei originating from two or more types of biological cells, and thus the analysis can be used to determine the amount of nucleic acid in respect of each of the cell type present in the sample. It has been observed that the area of T-cells (Jurkat) is 3-4 times smaller than the area of U2OS cell nuclei. The area of MCF-7 cell nuclei is between the area of the T-cell nuclei and the U2OS cell nuclei.

Magnification

It has surprisingly been found that it is possible to detect the signals from the labelled nuclei, even at a rather small magnification.

In an embodiment of the invention, the enlargement due to a magnification when examining the cells and/or nuclei is from relatively small to very small. Thus, it is often preferred that the spatial representation exposed onto the array of detection elements is subject to such a linear enlargement that the ratio of the image of a linear dimension on the array of detection elements to the original linear dimension in the exposing domain is smaller than 40:1, normally at the most 20:1, preferably smaller than 10:1 and in many cases even at the most 6:1 or even smaller than 4:1, such as smaller than 2:1 e.g. smaller than 1:1, such as smaller than 1:2. Preferred is a ration of about 4:1, 2:1 and 1:1.

The advantages of such low magnification are several, among other things increased area of observation and increased depth of focusing implying increased volume exposed to the detection device.

Statistics

The size of the sample volume analysed by fluorescence at one time is suitably adapted to the desired statistical quality of the determination. Thus, where the determination is the determination of the number of nuclei in a volume, or the determination of the size and/or shape of nuclei, the size of the volume of the liquid sample is preferably sufficiently large to allow identification therein of at least two of the nuclei. More preferably, the size of the volume of the liquid sample is sufficiently large to allow identification therein of at least four of the nuclei. This will correspond to a repeatability error of approximately 50%. Still more preferably, the size of the volume of the liquid sample is sufficiently large to allow identification therein of at least 10 of the nuclei. This will correspond to a repeatability error of approximately 33%. Even more preferably, the size of the volume of the liquid sample is sufficiently large to allow identification therein of at least 50 of the nuclei. This will correspond to a repeatability error of approximately 14%. Evidently, where possible, it is preferred to aim at conditions where the size of the volume allows identification of even higher numbers. Thus, when the size of the volume of the liquid sample is sufficiently large to allow identification therein of at least 100 of the nuclei, it will correspond to a repeatability error of approximately 10%, and when the size of the volume of the liquid sample is sufficiently large to allow identification therein of at least 1000 of the nuclei, it will correspond to a repeatability error of as low as approximately 3%.

Stand Still

In a preferred embodiment of the invention the nuclei being under determination for the amount of labelled nucleic acid are at stand still or substantially at stand-still during analysis, thus allowing the optimal use of measurement time in order to improve any signal to noise conditions. This arrangement also eliminates any error which could be inherent in the determination and/or assessment of nuclei caused by variation in flow conditions.

The volume of sample analysed when determining the amount of labelled nucleic acid within the nuclei, is in the range of 0.1-500 μL, more preferably 0.1-400 μL, further preferably 0.1-300 μL, even more preferably 0.1-200 μL, most preferably 0.2-100 μL.

Analysing Cells Based on the Content of Nucleic Acid

Analysis of the results obtained when determining the content of labelled nucleic acid of the nuclei analysed can be performed in a fluorescence microscopy with digital imagery. Examples of the analysis based on digital imagery are given in the examples 1-5 presented herein. The analysis of the results may be used for different purposes, some of these are quantification of nucleic acid, analysing the cell cycle status, determining the ploidy or determining the effect of drug interference on the cell cycle.

The method as described herein can be for quantification of nucleic acid of at least one biological cell, and comprise the steps of Providing a sample comprising at least one biological cell, or providing a sample comprising cell parts with nucleic acid, said cell parts being obtained from at least one biological cell, Adding an acidic agent to the sample causing acidification of the sample, Adding a detergent to the sample causing lysis of the biological cell, Adding a labelling agent to the sample, wherein the labelling agent interacts with nucleic acid, obtaining a sample with labelled nucleic acid, Determining the content of labelled nucleic acid of the at least one biological cell or cell parts in the sample.

The method described above can be amended to be used for analysing the cell cycle status of at least one biological cell, this method comprises the steps of Providing a sample comprising at least one biological cell, or providing a sample comprising cell parts with nucleic acid, said cell parts being obtained from at least one biological cell, Adding an acidic agent to the sample causing acidification of the sample, Adding a detergent to the sample causing lysis of the biological cell, Adding a labelling agent to the sample, wherein the labelling agent interacts with nucleic acid, obtaining a sample with labelled nucleic acid, Determining the content of labelled nucleic acid of the at least one biological cell or cell parts in the sample, Based on the content of labelled nucleic acid of the at least one biological cell or cell parts in the sample determine the cell cycle status.

The method for analysing the cell cycle status of at least one biological cell may further comprise any of the features described herein.

The method can also be amended to a method for determining the ploidy of at least one biological cell, this method comprises the steps of Providing a sample comprising at least one biological cell, or providing a sample comprising cell parts with nucleic acid, said cell parts being obtained from at least one biological cell, Adding an acidic agent to the sample causing acidification of the sample, Adding a detergent to the sample causing lysis of the biological cell, Adding a labelling agent to the sample, wherein the labelling agent interacts with nucleic acid, obtaining a sample with labelled nucleic acid, Determining the content of labelled nucleic acid of the at least one biological cell or cell parts in the sample, Based on the content of labelled nucleic acid of the at least one biological cell or cell parts in the sample determine the ploidy of the at least one biological cell.

The method for determining the ploidy of at least one biological cell may further comprise any of the features described herein.

The method can furthermore be amended to a method for determining the effect of drug interference on the cell cycle, the method comprising the steps of Providing a sample comprising at least one biological cell, or providing a sample comprising cell parts with nucleic acid, said cell parts being obtained from at least one biological cell, wherein said at least one biological cell has been exposed to an amount of a drug before sampling, or after sampling, Adding an acidic agent to the sample causing acidification of the sample, Adding a detergent to the sample causing lysis of the biological cell, Adding a labelling agent to the sample, wherein the labelling agent interacts with nucleic acid, obtaining a sample with labelled nucleic acid, Determining the content of labelled nucleic acid of the at least one biological cell or cell parts in the sample, Based on the content of labelled nucleic acid of the at least one biological cell or cell parts in the sample determine in what stage of the cell cycle the drug has interfered the cell cycle of the at least one biological cell.

The method for determining the effect of drug interference on the cell cycle of at least one biological cell may further comprise any of the features described herein.

The different methods described above are all based on determining the amount of nucleic acid present in the nuclei analysed. The assessment of the amount of the nuclei acid is based on the knowledge of the cell cycle of cells.

The S phase (synthesis phase) is a period in the cell cycle during interphase, between $G_1$ phase and the $G_2$ phase. Following $G_1$, the cell enters the S stage, where DNA synthesis or replication occurs. At the beginning of the S stage, each chromosome is composed of one coiled DNA double helix molecule (chromatid). The enzyme DNA helicase splits the DNA double helix. Then DNA polymerase splits the DNA strand, making two new semi-conservative strands. At the end of this stage, each chromosome has two identical DNA double helix molecules, and thus is composed of two sister chromatids (joined at the centromere). The end result of the S phase is the existence of duplicated genetic material in the cell, which will eventually be divided into two cells.

The $G_1$ phase is a period in the cell cycle during interphase. The $G_1$ phase occurs before the S phase. For many cells the $G_1$ phase is the major period of cell growth during its lifespan. A rapidly dividing human cell which divides every 24 hours spends 9 hours in $G_1$ phase. During the $G_1$ phase new organelles are synthesized. $G_1$ consists of four subphases:

A cell may pause in the $G_1$ phase before entering the S phase. A cell can also enter a state of dormancy called the $G_0$ phase. Most mammalian cells do this. In order to divide, the cell re-enters the cycle in S phase.

The DNA amount in a $G_1$ diploid eukaryotic cell is 2n, meaning there are two sets of chromosomes present in the cell. The genetic material exists as chromatin and if it were coiled into chromosomes, there would be no sister chromatids. Haploid organisms such as some yeasts will be 1 n and thus have only one copy of each chromosome present.

$G_2$ phase is the third, final, and usually the shortest subphase during interphase. In $G_2$ the cell undergoes a period of rapid growth to prepare for mitosis. It follows successful completion of DNA synthesis and chromosomal replication during the S phase, and occurs during a period of often four to five hours (for human cells). This far into interphase the nucleus is well defined, bound by a nuclear envelope and contains at least one nucleolus. Although chromosomes have been replicated they cannot yet be distinguished individually because they are still in the form of loosely packed chromatin fibers. The $G_2$ phase prepares the cell for mitosis (M phase) which is initiated by prophase.

At the end of the $G_2$ phase is a control checkpoint ($G_2$ checkpoint), where it is determined if the cell can proceed to enter M phase and divide. The $G_2$ checkpoint prevents cells from entering mitosis with DNA damaged since the last division, providing an opportunity for DNA repair and stopping the proliferation of damaged cells. Because the $G_2$ checkpoint helps to maintain genomic stability, it is an important focus in understanding the molecular causes of cancer.

The methods presented herein can be used to evaluate the cell cycle stage of the biological cells present in the obtained sample. Cells can be treated with drugs before or after obtaining a sample, and the cell cycle stage in which the cells are stopped by the drug can be determined as an assessment of the amount of nucleic acid present in analyzed nuclei of the treated cells.

Example 6 as described below illustrates that the method can be used determining the effects of drugs interfering with the cell cycle.

Kit of Parts

An aspect of the invention relates to a kit of parts for use in a method as described elsewhere herein, the kit comprises
  A volume of an acidic agent,
  A volume of a detergent,
  A volume of a labelling agent capable of interacting with nucleic acid, and
  Optionally a volume of a neutralization agent.

Each of the components can be present in at container i.e. in a container for an acidic agent, a container for a detergent, a container for a labelling agent and/or a container for a neutralization agent. The kit may thus comprise a container with an acidic agent, a container with a detergent, a container with a labelling agent and/or a container with a neutralization agent The volume of a detergent can be
present in the volume of an acidic agent or
separate from the volume of an acidic agent, the volume of labelling agent and the volume of a neutralization agent.

The detergent can thus be mixed with the acidic agent and be present in the container for an acidic agent. The detergent can also be separate from the other components in its own container.

In a preferred embodiment components of the kit are all in a liquid form i.e. the volume of an acidic agent, the volume of a detergent, the volume of a labelling agent and the volume of a neutralization agent all are in liquid form.

The volume of the acidic agent may be in the range of 5 μL to 10 mL, more preferable 10 μL to 8 mL, further preferable 20 μL to 7 mL, such as 30 μL to 6 mL, e.g. 40 μL to 5 mL, such as 50 μL to 6 mL, e.g. 60 μL to 5 ml, such as 70 μL to 4 mL, e.g. 80 μL to 3 mL. Most Preferred is a volume of 100 μL to 2.5 mL The features described elsewhere herein in respect of the acidic agent, the detergent, the labelling agent and the neutralization agent also concern these compositions when being part of a kit. The features are e.g. concentrations of the compositions, kinds of chemical compositions, pH-value.

The volume of the detergent, when being separate from the volume of an acidic agent, can be 5 μL to 1 mL, more preferable 5-750 μL, further preferable 5-500 μL, even further preferable 5-250 μL, most preferable 5 μL to 125 μL.

The volume of a labelling agent may in the kit be
  an integrated part of the to the volume of an acidic agent,
  an integrated part of the volume of the neutralisation agent, or
  separate from the volume of an acidic agent, and the volume of a neutralization agent.

In the kit the labelling agent may thus be present in the container for an acidic agent, in the container for a neutralisation agent or be present in the container for a labelling agent.

The labelling agent may be any labelling agent described elsewhere herein. The concentration and other features of the labelling agent described elsewhere herein also concerns the labelling agent of the kit. These features are e.g. the types of dyes and concentration of dyes.

The kit may comprise any neutralization agent as described elsewhere herein. The concentration and other features of the neutralization agent described elsewhere herein also concerns the neutralization agent of the kit. These features are e.g. the types of the neutralization agent, pH-values, and concentration of neutralization agent.

In the kit the amount of the neutralisation agent may be in the range of 5 μL to 10 mL, such as 10 μL to 9 mL, e.g. 20 μL to 8 mL, such as 30 μL to 7 mL, e.g. 40 μL to 6 mL, such as 50 μL to 5 mL, e.g. 60 μL to 4.5 mL, such as 70 μL to 4 mL, e.g. 80 μL to 3.5 mL, such as 90 μL to 3 mL. Preferred is a volume of 100 μL to 2.5 mL.

The kit may further comprise a volume of an RNase or a DNase. The features of the RNase and DNase may be anyone as described elsewhere herein.

The kit may also comprising instructions for use of the kit. The instructions may be included in a leaflet. The instructions may comprise a description of the order of adding the components to the sample as well as a description of the amount of the components to be used when performing the method. The instructions may also comprise a description of how to assess the results obtained when measuring the amount of nucleic acid of nuclei.

The kit may also comprise a cassette or slide for performing the reactions between the sample and the reagents and/or for analysing the reacted sample. The cassette or slides may be as described elsewhere herein. Preferred is a kit as described herein above further comprising at least one slide, such as at least two slides, e.g. at least three slides, such as at least four slides, e.g. at least five slides, such as at least six slides, e.g. at least seven slides.

The kit of parts may also comprise the composition for lysing and labelling biological cells, as described herein below. Especially the composition comprises
  An acidic agent or an acid buffer,
  A detergent and
  A labelling agent.

This composition may comprise any of the features of the acidic agent (or acid buffer), the detergent and the labelling agent as described elsewhere herein.

The kit of parts may also comprise the composition for labelling biological cells and simultaneously neutralising a sample comprising the biological cells, where this composition is further described below. The composition comprises
  A labelling agent and
  A neutralisation agent.

This composition may comprise any of the features of the labelling agent and the neutralisation agent as described elsewhere herein.

In a preferred embodiment the kit comprises a container with the composition for lysing and labelling biological cells and a container with the composition for labelling biological cells and simultaneously neutralising a sample comprising the biological cells. In a further preferred embodiment the kit comprises a container with the composition for lysing and labelling biological cells and a container with a neutralisation agent.

Slides

It is possible to perform the determination of the amount of labelled nucleic acid within the nuclei by locating the sample with the nuclei on a slide with chambers for the sample to analyse.

The slide may be a glass slide, e.g. a disposable glass slide. The slides can also be produced from a polymeric material, preferred is a polymeric material which do not absorbs ultraviolet light and violet light. An example of a suitable polymer is PMMA (Poly(methyl methacrylate)). Glas slides are normally prepared from glas types such as "Soda lime silica" (also used for windows) eller "borosilicate glass" (also used for laboratory glass equipment). Preferred glass slides are the glass slides "Fused quartz slides" which have an effective transmission of UV and violet light.

The dimensions of the slides are can be any suitable, and may be dependent of the input slide of the apparatus for performing the analysis of the cell nuclei, preferably the dimensions of the slides are 75 mm×25 mm×1 mm.

Each slide has a number of chambers for location of the sample to be analysed by fluorescence technique. The number of chambers on each slide may be 1, 2, 3, 4, 5, 6, 7, 8, 9, 10 or more than 10. Preferred numbers of chambers on each slide are 2, 4 or 8.

Each chamber of a slide may have a size suitable for containing a volume of the sample. The size of each chamber can be in the range of 1 μL to 100 μL, preferably 2 μL to 75 μL, more preferably 3 μL to 50 μL, further preferably 4 μL to 40 μL, most preferably 5 μL to 35 μL.

In a preferred embodiment each chamber of a slide has a width which is a little shorter than the width of the slide e.g. 23 mm, a length or 7-30 mm depending on the number of chambers in each slide and a depth of 0.02-0.1 mm.

Preferably, in slides with 2 or more chambers the chambers are located in a single row, as each chamber preferably has a width just a little shorter than the width of the slide. In a preferred embodiment cell nuclei of a single chamber are analysed at a time. This analysis can be performed on only a fraction of the area of the chamber, such as of about 90% of the area, e.g. about 80%, such as about 70%, e.g. about 60%, such as about 50%, e.g. about 40%.

In a preferred embodiment the dept of focus when measuring the amount of nucleic acid with the cell nuclei is suitable to analyse all the cell nuclei in the Z-plane i.e. in the depth of the chamber, which preferably is 0.02-0.1 mm.

In a slide with two or more chambers, the chambers can be used for examination of cell nuclei originating from a single sample. More preferably a single chamber is used for examination of cell nuclei origination from a single sample. However, in cases where the number of nuclei in a sample is expected to be very low, more than one chamber is used for examining cell nuclei from a single sample.

Slides suitable to use for the determination of the amount of labelled nucleic acid in cell nuclei, are slides which can be analysed by a NucleoCounter NC-3000 from ChemoMetec. The apparatus NucleoCounter NC-3000 is further described in PCT/DK2009/050278.

An aspect of the invention relates to a method for quantification of nucleic acid of at least one biological cell in a slide as described elsewhere herein, i. Providing a sample comprising at least one biological cell, or providing a sample comprising cell parts with nucleic acid, said cell parts being obtained from at least one biological cell, ii. Providing a cassette or slide as described elsewhere herein, iii. Adding an acidic agent, a detergent, a labelling agent to the sample causing acidification, lysis and labelling of the sample iv. optionally adding a neutralisation agent to the sample causing neutralisation of the sample, v. Guiding at least part of the acidified sample into the cassette or into chambers of the slide, and vi. Determining the content of labelled nucleic acid of the at least one biological cell or cell parts in the sample while the cell nuclei with labelled nucleic acid are present in the cassette or in a chamber of the slide.

System for Analysing the Labelled Sample

The method according to the invention for determining the amount of nucleic acid of cells of a biological sample may be conducted in any suitable system and apparatus.

The method according to the invention may be performed by monitoring in a microscope, in a flow cytometer, or in a cell counting devices such as instruments from ChemoMetec NS.

Measurements may be performed in cell counting devices such as instruments from ChemoMetec NS, such as provided by the NucleoCounter family of instruments from ChemoMetec NS, hereunder using low magnification and/or optionally disposable cassettes or slides or other sample compartments (c.f., e.g., Hansen, F. E. R., Glensbjerg, M., Arnvidarson, B. & Jeppesen, J. M.: "A Method and a System for Determination of Cells in a Liquid", PCT/DK1998/0000175 (WO/1998/050777).

In a preferred embodiment the determination of labelled nucleic acid is conducted in a system comprising a sample domain or a chamber wherein the sample is arranged and signals from the labelled nucleic acid are detected and analysed Especially suited for performing the determination of the quantity of labelled nucleic acid in the nuclei obtained from the sample, may be a fluorescence microscope with imaging software. Especially some of the products of the Nucleo-Counter family of ChemoMetec are suitable for performing the quantification of labelled nucleic acid and performing the analysis. The NucleoCounter instruments are fast, precise and objective and they requires no calibration, cleaning or maintenance, hereby making it easy to obtain good and precise results in a simple way due to a fast, precise and objective analysis of the nucleic acid of the nuclei. The NucleoCounter Instruments are based on fluorescence microscopy by combining a fluorescence microscope with a CCD camera and image analysis in a single portable unit. The fluorescence microscope is designed to detect signals from fluorescence dyes which stain the DNA and/or RNA of cell nuclei.

In a preferred embodiment the method described herein is performed such that the step of determining the amount of labelled nucleic acid of cell nuclei is performed by positioning a sample of the labelled cell nuclei into the chambers of a slide described herein above, the slide is entered into a NucleoCounter NC-3000, which perform the determination of the amount of labelled nuclei acid in the cell nuclei, and this apparatus also perform an analysis of the results obtained.

An apparatus for determining the amount of labelled nucleic acid of cell nuclei may comprise different light sources for excitation of the label used for labelling the nucleic acid in a cell nuclei and/or different emission filters making it possible to obtain good images of the light emitted from the excited labelled nucleic acid.

Light sources of the apparatus may excite light with peaks at e.g. 365, 405, 455, 475, 500, 525 or 590 nm. Emission filters may allow light with the following wave length to pass the filter 410-450, 415-525, 450-500, 500-555, 520-595, 555-605, 595-750, 630-1100 nm. The exciting light and emission filter are selected in relation to the label used for labelling the nucleic acid.

When determining the amount of labelled nucleic acid an optical magnification of 40× or less can be used, preferably 20× or less, more preferably 10× or less, such as 6× or less, such as 4× or less, such as 2× or less. Preferably the magnification is non-existing i.e. 1 or as little as 2× or 4×. Preferred is also magnifications below 1 e.g. 0.75×, 0.5× and 0.25×. Of these magnifications below 1, 0.75× is preferred and 0.5× is more preferred.

The method as described herein makes it possible to obtain a good image without too much noise at a low magnification. Hereby it is possible to analyse a statistically representative number of cell nuclei in a very short time.

The analysis time can be as low as less than 1 min when analysing 10 µL of sample. Preferably the analysis of sample within a single chamber is analysed within 10 sec, such as within 5 sec.

Compositions

An aspect of the invention relates to a composition for lysing and labelling biological cells, said composition comprising
An acidic agent or an acid buffer,
A detergent and
A labelling agent.

This composition may comprise any of the features of the acidic agent (or acid buffer), the detergent and the labelling agent as described elsewhere herein. A preferred composition comprises: Acidic agent: Citrate buffer (pH 2.25, 100 mM), Detergent: Triton X-100 (0.5%), and Fluorochrome: DAPI (5 µg/mL).

Another aspect of the invention relates to a composition for labelling biological cells and simultaneously neutralising a sample comprising the biological cells, said composition comprising
A labelling agent and
A neutralisation agent.

This composition may comprise any of the features of the labelling agent and the neutralisation agent as described elsewhere herein. A preferred composition comprises: Neutralisation agent: Citrate buffer (pH 8.3, 500 mM), Fluorochrome: DAPI (5 µg/mL)

Use

A preferred use is the use of the kit-of-parts as described elsewhere herein in a method for quantification nucleic acid of at least one biological cell. This quantification of nucleic acid may be used for any assessment as described herein.

An aspect of the invention relates to the use of the method as described herein or of the kit as described herein for examining whether a biological sample includes genomically unstable cells.

An analysis of genomically unstable cells may be used with a biological sample which is a blood sample or a tissue sample.

Surveillance of Disease Development

An aspect of the invention relates to a method for analysing the development of a disease causing unstable cells of an individual, where the method comprises the steps of, at two different points of time Obtaining a biological sample from an individual,
Analysing the obtained biological sample for the presence of unstable cells e.g. genomically unstable cells,
Comparing the number of unstable cells identified in the biological sample at the two different points of time,
Determining the development of the disease based on the comparison of the number of unstable cells e.g. genomically unstable cells identified in the two biological samples.

When comparing the results obtained from two different samples obtained at different times from the same individual, it may be possible to evaluate any development of a disease or an improved status of an individual having a disease.

The two different points of time can be separated by at least 24 hours. A point of time is a time where a sample is obtained from an individual. Samples can be obtained with an interval of at least 1 day, such as at least 2 days, e.g. at least 3 days, such as at least 4 days, e.g. at least 5 days, such as at least 6 days, e.g. at least 1 week, such as at least 2 weeks, e.g. at least 3 weeks, such as at least 4 weeks, e.g. at least 5 weeks, such as at least 6 weeks, e.g. at least 7 weeks, such as at least 8 weeks, e.g. at least 9 weeks, such as at least 10 weeks, e.g. at least 11 weeks, such as at least 12 weeks, e.g. at least 13 weeks, such as at least 14 weeks, e.g. at least 15 weeks.

The biological sample obtained and analysed for the existence of unstable cells e.g. genomically unstable cells may be a blood sample or a tissue sample.

The diseases where detection of unstable cells e.g. genomically unstable cells may be important can be in respect of a cancer disease. The cancer may be Lymphoma, Melanoma, Leukemia and Bladder, Breast, Colon and Rectal, Endometrial, Kidney (Renal Cell), Lung, Pancreatic, Prostate Skin (Nonmelanoma), or Thyroid cancer.

DETAILED DESCRIPTION OF THE DRAWINGS

FIG. 1 illustrates DNA content profiles of nuclei released by acid lysis and stained with DAPI. Released nuclei were either directly analysed (Acid lysis) or neutralized by adding stabilization buffer (Acid lysis+neutralization) prior to analysis. Fluorescence was measured by quantitative imaging cytometry using a Nucleocounter NC-3000 (Chemometec). Left panel, images captured by NC-3000 (2× magnification); Right panel, DNA content histograms obtained from the Nucleoview NC-3000 software displaying fluorescence intensity as a function of cell number.

Figure 2:
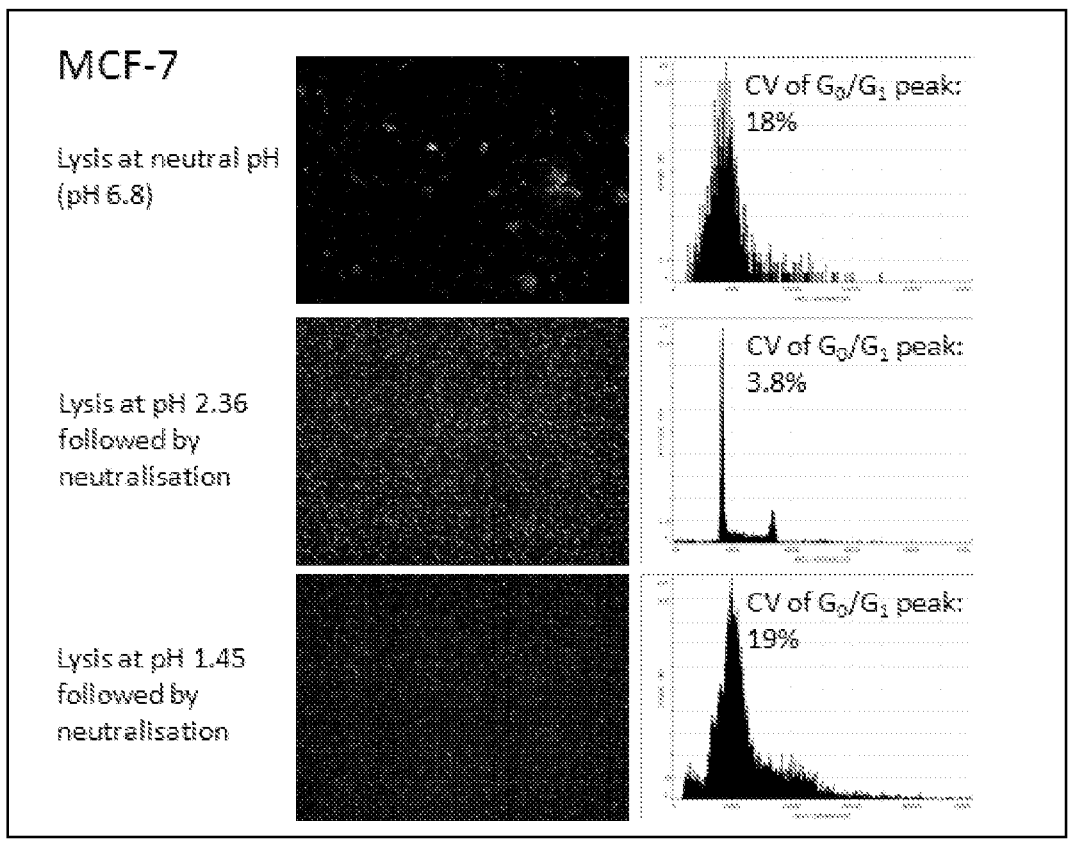
FIG. 2 illustrates DNA content profiles of DAPI stained nuclei from MCF-7 cells lysed at different pH-values.

FIG. 2 illustrates DNA content profiles of DAPI stained nuclei from MCF-7 cells. Fluorescence was measured by quantitative imaging cytometry using a Nucleocounter NC-3000 (Chemometec). Upper panel: Nuclei released at neutral pH; Middle panel, nuclei released at pH 2.36; lower panel, nuclei released at pH 1.45. Left panel, images captured by NC-3000 (2× magnification); Right panel, DNA content histograms obtained from the Nucleoview NC-3000 software displaying fluorescence intensity as a function of cell number.

Figure 3:
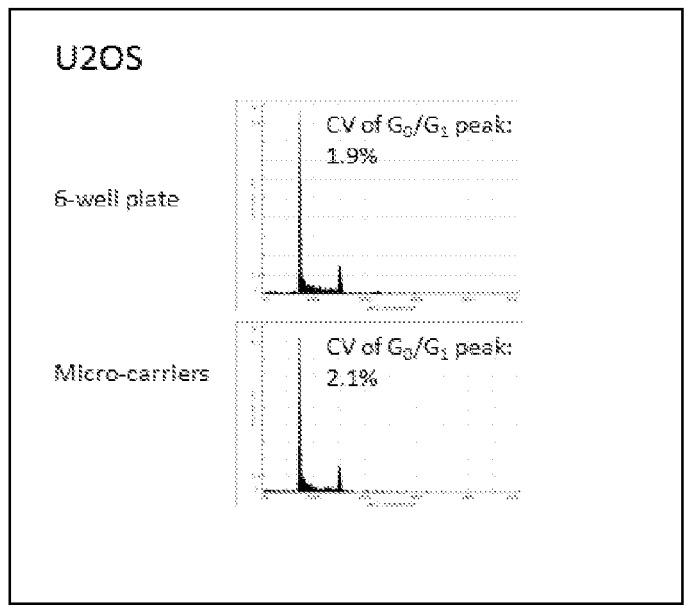
FIG. 3 illustrates DNA content profiles of DAPI stained nuclei from U2OS cells adhered to different substrates.

FIG. 3 illustrates DNA content profiles of DAPI stained nuclei from U2OS cells. Fluorescence was measured by quantitative imaging cytometry using a Nucleocounter NC-3000 (Chemometec). DNA content histograms were obtained from the Nucleoview NC-3000 software and display fluorescence intensity as a function of cell number. Upper panel: U2OS cells grown in 6-well plates; lower panel, U2OS grown on microcarriers maintained in spinner flasks.

Figure 4:
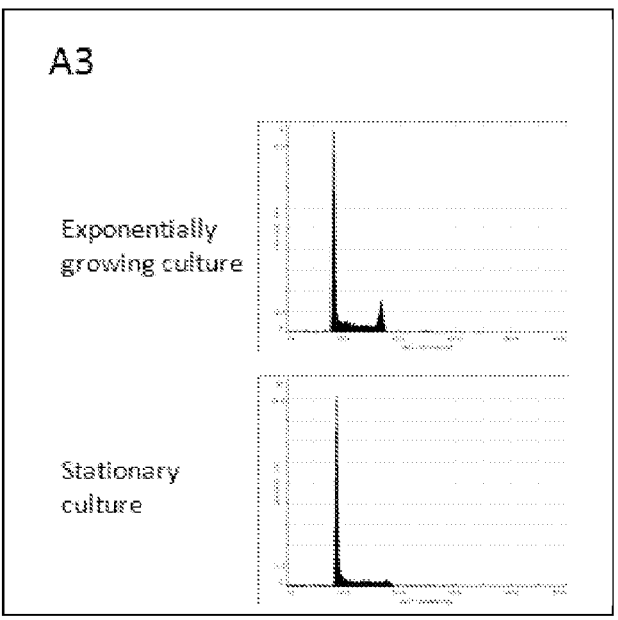
FIG. 4 illustrates DNA content profiles of DAPI stained nuclei from A3 cells in different growth phases.

FIG. 4 illustrates DNA content profiles of DAPI stained nuclei from A3 cells. Fluorescence was measured by quantitative imaging cytometry using a Nucleocounter NC-3000. DNA content histograms were obtained from the Nucleoview NC-3000 software and display fluorescence intensity as a function of cell number. Upper panel: exponentially growing A3 cells; lower panel, A3 cells grown to stationary phase.

Figure 5:
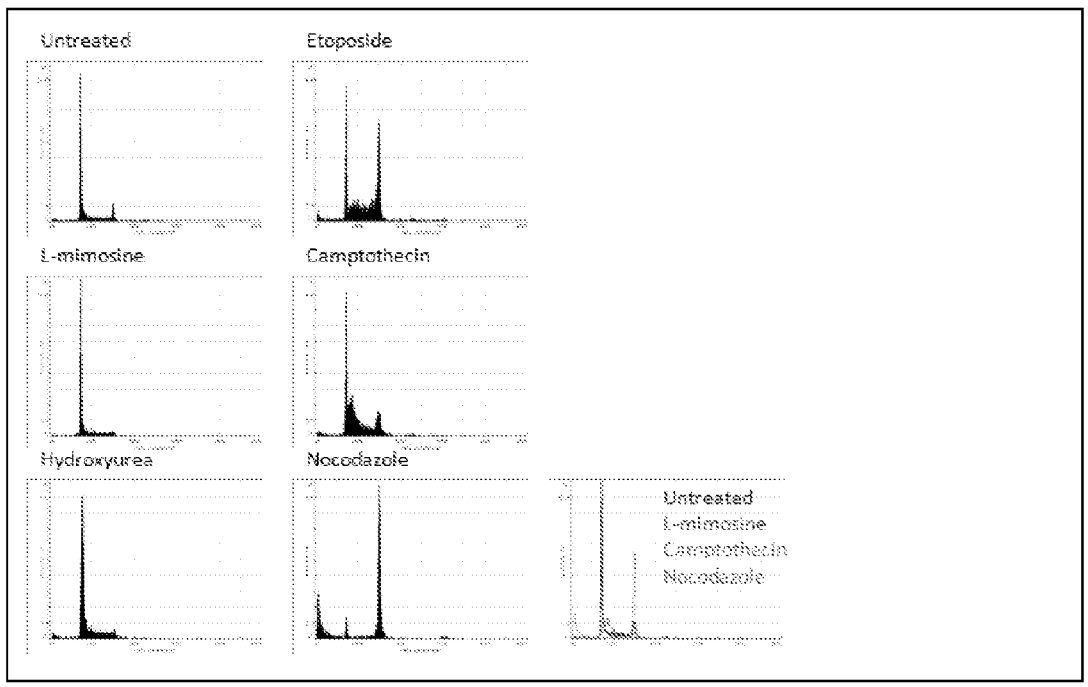
FIG. 5 illustrates DNA histograms of U2OS cells treated with different drugs.

FIG. 5 illustrates DNA histograms of U2OS cells treated with different drugs. Fluorescence was measured by quantitative imaging cytometry using a Nucleocounter NC-3000. DNA content histograms were obtained from the Nucleoview NC-3000 software and display fluorescence intensity as a function of cell number. Histogram in lower right corner is the result of merging untreated, L-mimosine, camptothecin and nocodazole treated samples.

EXAMPLES

The method of the present invention has been evaluated by quantification of cellular DNA. Several aspects of the method has been analysed, as is explained in the examples presented below.

Example 1

Nuclei Released by Acid Lysis and Used for Accurate and Precise DNA Quantification The DNA content of three adherent cell lines, CHO, MCF-7 and U2OS was measured by staining nuclei released by acid lysis with DAPI (4',6-diamidino-2-phenylindole).
Materials and Methods:

Adherent cell lines were grown in RPMI+10% FCS to 80-90% confluency in T25 flasks. To release nuclei directly from the attached cells, T25 flasks were washed once with 5 mL of PBS and then incubated in presence of 0.65 ml of lysis buffer (50 mM citric acid (pH 2.20), 1% Triton X-100, 1 µg/ml DAPI) at 37° C. for 5 minutes. The fluorescence of the released nuclei were either directly analysed by quantitative imaging cytometry or neutralized by adding equal amounts (0.65 ml) of stabilization buffer (250 mM citrate (pH 8.3), 1% Triton X-100) prior to imaging. Quantitative imaging cytometry was performed using a Nucleocounter NC-3000 (Chemometec)
Results:

It was tested whether nuclei released using acid lysis could be homogenously stained with the DNA specific dye DAPI. MCF-7, U2OS and CHO cells (all adherent cell lines) were treated with an acidic lysis buffer supplemented with Triton X-100 and DAPI. Acid released nuclei were either directly analysed by quantitative imaging cytometry or neutralized by adding stabilization buffer prior to imaging. As shown in FIG. 1 it is possible to obtain acceptable DNA content profiles of cells directly analysed after acid released lysis. However, the coefficient of variance (CV) of the $G_1/G_0$ peak was broad (≥10%) for all cell lines indicating some inaccuracy of the method. Next, it was tested whether neutralization of the acid released nuclei could improve the accuracy. For all the tested cell lines neutralization improved the DNA quantification considerably and the CV's of the $G_1/G_0$ peak were in the range of 3.4 to 4.9%.

No or very little aggregation of the released nuclei was observed by imaging the sample (FIG. 1, left panel).

To conclude, release of nuclei by acid lysis provides a very fast and simple method for quantifying cellular DNA content. Combined with neutralisation the method also offers very high accuracy and precision. The method completely circumvents the need for trypsination of samples comprising adherent cells.

FIG. 1 illustrates DNA content profiles of DAPI stained nuclei from CHO, U2OS and MCF-7 cells obtained by acid lysis. Released nuclei were either directly analysed (Acid lysis) or neutralized by adding stabilization buffer (Acid lysis+neutralization) prior to analysis. Fluorescence was measured by quantitative imaging cytometry using a Nucleocounter NC-3000 (Chemometec). Left panel, images captured by NC-3000 (2× magnification); Right panel, DNA content histograms obtained from the Nucleoview NC-3000 software displaying fluorescence intensity as a function of cell number.

Example 2

Determining the Optimal pH for Nuclei Release, De-Aggregation and Homogeneous DNA Staining The three adherent cell lines, CHO, MCF-7 and U2OS were used for determining the optimal pH for the following three parameters:
1) Efficient release of nuclei (>90 release of nuclei from attached cells)
2) Little or no aggregation of the released nuclei
3) Homogeneous DNA staining providing high accuracy and precision of DNA content measurements Materials and Methods:

Adherent cell lines were grown in RPMI+10% FCS to 80-90% confluency in 6-well plates (Nunclon surface, Nunc). To release nuclei directly from the attached cells, each of the wells was washed once with 1 mL of PBS and then incubated in the presence of 0.25 ml of lysis buffer (0.5% Triton X-100, 1 µg/ml DAPI dissolved in either, 200 mM citric acid (pH 2.00), 100 mM citrate buffer (pH 2.22-6.80) or 400 mM phosphoric acid (pH 1.45) at 37° C. for 5 minutes. The released nuclei were neutralized by adding 0.25 ml stabilization buffer (100 or 200 mM citrate, pH 8.3). For details about the experimental conditions see table 1, which illustrates the effects of pH on release of nuclei, aggregation and DNA quantification. The fluorescence of the nuclei was analysed by image cytometry using a Nucleocounter NC-3000 (Chemometec)
Results:

Cell attached to the bottom of plastic wells was incubated briefly with different buffers having pH's spanning from pH 1.45 to 6.8 and supplemented with DAPI and Triton X-100. Released nuclei were neutralised by adding citrate (pH 8.3) and removed from the well. Subsequently, the bottom of the well was inspected in an inverted microscope to estimate the efficiency of nuclei release. In general pH should be below 2.75 for efficient release of nuclei (>90% of the cell population has been lysed and their nuclei is released to the solution). Next, the released and neutralized nuclei was analysed by quantitative image cytometry. Imaging of the samples revealed that if the pH of the lysis buffer is below approximately 3.0 aggregation of the nuclei is prevented (Table 1, FIG. 2). However, quantification of DNA content revealed that pHs below 2.2 compromise the quality of the DNA staining, resulting in broad $G_1/G_0$ peaks with high coefficient of variance (Table 1). Moreover, very low pH promotes DNA degradation resulting in nuclei with less than 1 DNA equivalents (FIG. 2). Too harsh pH may cause depurination, triggering destabilization and fragmentation of the DNA.

To conclude, in order to obtain efficient release of nuclei, without aggregation and at the same time achieving highly homogeneous DNA staining the pH of the lysis solution has to be kept within the range of 2.2-2.8.

release nuclei directly from the attached cells, each of the wells was washed once with 1 mL of PBS and then incubated with 0.25 ml of lysis buffer (100 mM citrate buffer (pH2.25), 0.5% Triton X-100) in the presence or absence of DAPI for 5 minutes at ° 37 C. The released nuclei were neutralized by incubation with 0.25 ml stabilization buffer (500 mM citrate,

TABLE 1

Effects of pH on release of nuclei, aggregation and DNA quantification

| Cell type | pH | Lysis buffer | | | Neutralisation buffer | >90% release | Nuclei Aggregation | CV on | |
|---|---|---|---|---|---|---|---|---|---|
| | | Citrate buffer | Triton X-100 | DAPI | Sodium citrate | | | $G_1$ peak | DNA profile[1] |
| CHO | 2.02 | 200 mM | 0.5% | 1 μg/ml | 200 mM | Yes | No | 7.1 | (+) |
| CHO | 2.22 | 100 mM | 0.5% | 1 μg/ml | 100 mM | Yes | No | 6.3 | + |
| CHO | 2.36 | 100 mM | 0.5% | 1 μg/ml | 100 mM | Yes | No | 5.6 | + |
| CHO | 2.75 | 100 mM | 0.5% | 1 μg/ml | 100 mM | Yes | Yes | 6.2 | (+) |
| CHO | 3.02 | 100 mM | 0.5% | 1 μg/ml | 100 mM | Yes | Yes | 6.6 | (+) |
| CHO | 3.33 | 100 mM | 0.5% | 1 μg/ml | 100 mM | No | Yes | 5.5 | − |
| CHO | 3.57 | 100 mM | 0.5% | 1 μg/ml | 100 mM | No | Yes | 6.2 | − |
| CHO | 3.76 | 100 mM | 0.5% | 1 μg/ml | 100 mM | No | Yes | 6.3 | − |
| CHO | 3.94 | 100 mM | 0.5% | 1 μg/ml | 100 mM | No | Yes | 6.5 | − |
| CHO | 6.80 | 100 mM | 0.5% | 1 μg/ml | 100 mM | No | Yes | 7.7 | − |
| MCF-7 | 2.02 | 200 mM | 0.5% | 1 μg/ml | 200 mM | Yes | No | 6.1 | (+) |
| MCF-7 | 2.22 | 100 mM | 0.5% | 1 μg/ml | 100 mM | Yes | No | 4.5 | + |
| MCF-7 | 2.36 | 100 mM | 0.5% | 1 μg/ml | 100 mM | Yes | No | 3.8 | + |
| MCF-7 | 2.75 | 100 mM | 0.5% | 1 μg/ml | 100 mM | Yes | No | 3.8 | + |
| MCF-7 | 3.02 | 100 mM | 0.5% | 1 μg/ml | 100 mM | Yes | Yes | 4.5 | + |
| MCF-7 | 3.33 | 100 mM | 0.5% | 1 μg/ml | 100 mM | No | Yes | 4.4 | (+) |
| MCF-7 | 6.80 | 100 mM | 0.5% | 1 μg/ml | 100 mM | No | Yes | 18 | − |
| U2OS | 2.02 | 200 mM | 0.5% | 1 μg/ml | 200 mM | Yes | No | 6.3 | (+) |
| U2OS | 2.22 | 100 mM | 0.5% | 1 μg/ml | 100 mM | Yes | No | 4.6 | + |
| U2OS | 2.36 | 100 mM | 0.5% | 1 μg/ml | 100 mM | Yes | No | 4.8 | + |
| U2OS | 2.75 | 100 mM | 0.5% | 1 μg/ml | 100 mM | Yes | No | 4.1 | + |
| U2OS | 3.02 | 100 mM | 0.5% | 1 μg/ml | 100 mM | No | No | 5.8 | − |
| U2OS | 3.33 | 100 mM | 0.5% | 1 μg/ml | 100 mM | No | Yes | NA | − |
| U2OS | 6.80 | 100 mM | 0.5% | 1 μg/ml | 100 mM | No | Yes | NA | − |

NA = not applicable
[1]Sharp, discrete $G_1/G_0$ and $G_2$ peaks that are well separated from each other. +, Excellent; (+), Acceptable; −Unacceptable.

FIG. 2 illustrates DNA content profiles of DAPI stained nuclei from MCF-7 cells. Fluorescence was measured by quantitative imaging cytometry using a Nucleocounter NC-3000 (Chemometec). Upper panel: Nuclei released at neutral pH; Middle panel, nuclei released at pH 2.36; lower panel, nuclei released at pH 1.45. Left panel, images captured by NC-3000 (2× magnification); Right panel, DNA content histograms obtained from the Nucleoview NC-3000 software displaying fluorescence intensity as a function of cell number.

Example 3

Effects of DAPI Concentrations and Staining Procedure

The adherent cell line U2OS was used for testing whether the accuracy and precision of the DNA staining could be further improved by doing the nuclei staining in the neutralization step instead of the lysis step.
Materials and Methods:
U2OS cells were grown in RPMI+10% FCS to 80-90% confluency in 6-well plates (Nunclon surface, Nunc). To pH 8.3) in the presence or absence of DAPI for 5 minutes at ° 37 C. For details about the experimental conditions see table 2, which illustrates the effects of DAPI concentrations and staining procedure. The fluorescence of the nuclei was analysed by image cytometry using a Nucleocounter NC-3000 (Chemometec)
Results:
It was evaluated whether the method could be further improved by adding DAPI to the neutralization buffer instead of the lysis buffer. As shown in table 2 there is apparently no difference between doing the nuclei staining in the lysis step and in the neutralization step. In both cases the accuracy and precision of the DNA staining is high providing DNA content profiles with narrow $G_1/G_0$ peaks and remarkably low CV. Table 2 also demonstrates that the method is robust for variations in DAPI concentrations. Hence, DAPI concentrations in the range of 1-10 μg/ml allow specific and precise quantification of cellular DNA content.

TABLE 2

Effects of DAPI concentrations and staining procedure.

| Cell type | Lysing buffer pH | DAPI µg/ml | Neutralization buffer pH | DAPI µg/ml | >90% release | Aggregation | CV | $G_1/G_0$ peak Intensity | DNA profile[1] |
|---|---|---|---|---|---|---|---|---|---|
| U2OS | 2.25 | 1 | 8.3 | 0 | Yes | No | 2.1% | 118.000 | + |
| U2OS | 2.25 | 0 | 8.3 | 1 | Yes | No | 2.1% | 119.500 | + |
| U2OS | 2.25 | 5 | 8.3 | 0 | Yes | No | 2.3% | 127.000 | + |
| U2OS | 2.25 | 0 | 8.3 | 5 | Yes | No | 2.0% | 128.000 | + |
| U2OS | 2.25 | 10 | 8.3 | 0 | Yes | No | 2.1% | 125.000 | + |
| U2OS | 2.25 | 0 | 8.3 | 10 | Yes | No | 2.1% | 125.500 | + |

[1]Sharp, discrete $G_1/G_0$ and $G_2$ peaks that are well separated from each other. +, Excellent; (+), Acceptable; −Unacceptable Example 4

Cell Cycle Analysis on Cells Attached to Micro-Carriers Using Acid Lysis Method

The adherent cell line U2OS was used for testing whether the acid lysis method could be used for measuring the DNA profiles of cell growing on micro-carriers.
Materials and Methods:
U2OS cells were grown in RPMI+10% FCS to 80-90% confluency in 6-well plates (Nunclon surface, Nunc) or on Cytodex 3 microcarriers (GE healthcare) maintained in spinner flasks. To release nuclei from cells grown 6-well plates, each of the wells was washed once with 1 mL of PBS and then incubated with 0.25 ml of lysis buffer (100 mM citrate buffer (pH 2.25), 0.5% Triton X-100, 5 µg/ml DAPI) for 5 minutes at 37° C.
To release nuclei from cells attach to microcarriers, 2 ml of the sample was centrifuged for 5 minutes at 500 g, pelleted microcarriers were washed once with 1 ml of PBS, resuspended in 0.25 ml of lysis buffer (100 mM citrate buffer (pH 2.25), 0.5% Triton X-100, 5 µg/ml DAPI) and then incubated for 5 minutes at 37° C. Samples from 6-well plates and microcarriers were neutralized by adding 0.25 ml stabilization buffer (500 mM citrate, pH 8.3). The fluorescence of the released nuclei was analysed by image cytometry using a Nucleocounter NC-3000 (Chemometec).
Results:
U2OS cells were seeded and grown in parallel on Cytodex 3 microcarriers in spinnerflasks and in 6-well plates. At 80-90% confluency the cells were subjected to acid lysis and the released nuclei were neutralised with stabilization buffer. Next, the DNA profiles of the two samples were determined by image cytometry. As shown in FIG. 3 the DNA profile of the sample grown on microcarriers was nearly identical to that of the sample grown in a 6-well plate. It was tested and confirmed that close to 100% of the cell population was released from the microcarriers by microscopic examination. Hence, the acid lysis method provides a simple and reliable way of measuring DNA content of cell populations growing on microcarriers.
FIG. 3. illustrates DNA content profiles of DAPI stained nuclei from U2OS cells. Fluorescence was measured by quantitative imaging cytometry using a Nucleocounter NC-3000 (Chemometec). DNA content histograms were obtained from the Nucleoview NC-3000 software and display fluorescence intensity as a function of cell number. Upper panel: U2OS cells grown in 6-well plates; lower panel, U2OS grown on microcarriers maintained in spinner flasks.

Example 5

Cell Cycle Analysis on Suspension Cells Using Acid Lysis

Leukemic T lymphocytes, A3, (a derivative of the Jurkat cell line) were used for testing whether the acid lysis method could be used for measuring DNA profiles of cells in suspension.
Materials and Methods:
A3 cells were seeded at a density of $2.5 \times 10^5$ cells/ml in RPMI+10% FCS and maintained in a T-25 flask. 1 ml of the cell suspension was harvested after, respectively, 24 hours (exponentially growing cells) and 96 hours (stationary cells). Samples were centrifuged for 5 minutes at 500 g, supernatants were discarded and cells were resuspended in 0.25 ml of lysis buffer (100 mM citrate buffer (pH 2.25), 0.5% Triton X-100, 5 µg/ml DAPI). After 5 minutes of incubation at 37° C. 0.25 ml of stabilization buffer (500 mM citrate, pH 8.3) was added to the samples. The fluorescence of the released nuclei was analysed by image cytometry using a Nucleocounter NC-3000.
Results:
Using the acid lysis method the DNA content of, respectively, exponentially growing cells and stationary cells was measured for a suspension cell line (A3, Jurkat cell line). As illustrated in FIG. 4 the acid lysis method uncovers a significant difference between the two cell conditions; an exponentially growing Jurkat cell population has a clear $G_2$ peak, whereas a population of stationary Jurkat cells lacks $G_2$ cells, leaving the majority of the cells in the $G_1$ phase of the cell cycle. Hence, the acid lysis method allows a simple and reliable quantification of the DNA content of cells in suspension.
FIG. 4 illustrates DNA content profiles of DAPI stained nuclei from A3 cells. Fluorescence was measured by quantitative imaging cytometry using a Nucleocounter NC-3000. DNA content histograms were obtained from the Nucleoview NC-3000 software and display fluorescence intensity as a function of cell number. Upper panel: exponentially growing A3 cells; lower panel, A3 cells grown to stationary phase.

Example 6

Measurement of Drug Effects on Cell Cycle Using Acid Lysis Method

The DNA content of U2OS cells treated with different drugs was measured using the acid lysis method.

Materials and Methods:

U2OS cells were grown in RPMI+10% FCS to approximately 75% confluency in 6-well plates (Nunclon surface, Nunc) and then treated with the following drugs for 20 hours:

| | |
|---|---|
| 1. Nocodazole ($G_2$-M arrest): | 0.5 µM |
| 2. L-mimosine ($G_1$ arrest): | 0.5 mM |
| 3. Hydroxyurea, HU (S arrest): | 2 mM |
| 4. Camptothecin, CRT (S-$G_2$ arrest): | 5 µM |
| 5. Etoposide (S-$G_2$ arrest): | 20 µM |
| 6. Untreated control | |

After drug treatment each of the wells was washed once with 1 mL of PBS and then incubated with 0.25 ml of lysis buffer (100 mM citrate buffer (pH 2.25), 0.5% Triton X-100, 5 µg/ml DAPI) for 5 minutes at 37° C. Prior to quantitative image cytometry (Nucleocounter NC-3000), the samples were neutralized by adding 0.25 ml stabilization buffer (500 mM citrate, pH 8.3).

Results:

U2OS cells treated with drugs affecting different phases of the cell cycle were analysed using the acid lysis method. The cell cycle distributions were in line with the known effects of the drugs (FIG. 5). For example, L-mimosine is known to induce a $G_1$ arrest and evidently the sample treated with this drug displays a predominantly $G_1$ peak and very few cells are in the S and $G_2$-M phases of the cell cycle. Likewise, camptothecin has been described to induce an S-$G_2$ arrest in U2OS cells and indeed the sample treated with this drug has an accumulation of S-$G_2$ cells. In conclusion, the acid lysis method enables simple and reliable quantification of cellular DNA and can be used for evaluating the effects of different drugs on the cell cycle.

FIG. 5 illustrates DNA histograms of U2OS cells treated with different drugs. Fluorescence was measured by quantitative imaging cytometry using a Nucleocounter NC-3000. DNA content histograms were obtained from the Nucleoview NC-3000 software and display fluorescence intensity as a function of cell number. Histogram in lower right corner is the result of merging untreated, L-mimosine, camptothecin and nocodazole treated samples.

The invention claimed is:

1. A method for quantification of nucleic acid of biological cells, said method comprising the steps of:
   i. providing a sample comprising biological cells, or providing a sample comprising cell parts with nucleic acid, said cell parts being obtained from biological cells, wherein the method is performed without fixation of the biological cells;
   ii. adding an acidic agent to the sample, the acidic agent comprising a detergent in a buffer having a pH between 2.1-2.9 thereby causing lysis of the biological cells, release of nuclei and inhibition of aggregation of the nuclei;
   iii. adding a fluorescent labelling agent to the sample, wherein the fluorescent labelling agent interacts with nucleic acid, thereby obtaining a sample with fluorescent labelled nucleic acid;
   iv. adding a neutralization agent thereby neutralizing the sample after or simultaneously with adding the labelling agent;
   v. determining the content of fluorescent labelled nucleic acid within the released nuclei; and
   vi. assessing a result obtained by determining the content of fluorescent labelled nucleic acid to obtain information of the cells in respect of cell cycle analysis, wherein the pH between 2.1-2.9 provides a $G_1/G_0$ peak having a reduced coefficient of variance compared to a method in which the pH is lower or higher than 2.1-2.9.

2. The method according to claim 1, wherein the biological cells are prokaryotes or eukaryotes.

3. The method according to claim 1, wherein the acidic agent is selected from the group consisting of biological buffers of citric acid, citrate buffer, phosphoric acid, maleate, phosphate, glycine, glycylglycine, malate, lactate, formate, succinate, acetate and propionate.

4. The method according to claim 1, wherein the concentration of the buffer is 25-250 mM.

5. The method according to claim 1, wherein the pH of the acidified sample is kept under acidic conditions for about 1-30 minutes.

6. The method according to claim 1, wherein the detergent is ionic or non-ionic.

7. The method according to claim 1, wherein the detergent is used in an amount such that it constitutes 0.05%-5% (w/v) of the volume of the acidic agent used.

8. The method according to claim 1, wherein the neutralization agent is a buffer.

9. The method according to claim 1, wherein the neutralization agent has a pH between 7 and 9.

10. The method according to claim 1, wherein the neutralization agent is in a concentration of 50-1000 mM.

11. The method according to claim 1, wherein the fluorescent labelling agent is a fluorescent dye capable of interacting with nucleic acid.

12. The method according to claim 11, wherein the fluorescent dye is selected from the group of DNA specific fluorescent dyes and fluorescent dyes binding DNA and RNA.

13. The method according to claim 1, further comprising degrading RNA or DNA by adding RNase or DNase to the sample.

14. The method according to claim 1, further comprising assessing the result obtained when determining the content of fluorescent labelled nucleic acid of the cells or cell parts in the sample to obtain information of the cells in respect of ploidy determination, measurements of nucleotide incorporation and assays for proliferation, health, stress level, apoptosis, necrosis, or other state of conditions of cells.

15. The method according claim 1, further comprising the step of measuring the area of the nuclei.

16. The method according to claim 1, said method being performed without a hydrolysis of the nucleic acid or without trypsinization of the sample or of biological cell or cell parts of the sample.

17. The method of claim 1, wherein the acidic agent has a pH in the range of 2.2-2.8.

\* \* \* \* \*